US009139615B2

(12) United States Patent
Bach et al.

(10) Patent No.: US 9,139,615 B2
(45) Date of Patent: Sep. 22, 2015

(54) HIGH-AFFINITY, DIMERIC INHIBITORS OF PSD-95 AS EFFICIENT NEUROPROTECTANTS AGAINST ISCHEMIC BRAIN DAMAGE AND FOR TREATMENT OF PAIN

(75) Inventors: Anders Bach, Valby (DK); Kristian Stromgaard, Roskilde (DK)

(73) Assignee: University of Copenhagen, Copenhagen (DK)

( * ) Notice: Subject to any disclaimer, the term of this patent is extended or adjusted under 35 U.S.C. 154(b) by 0 days.

(21) Appl. No.: 14/116,862

(22) PCT Filed: May 11, 2012

(86) PCT No.: PCT/EP2012/058762
§ 371 (c)(1),
(2), (4) Date: Nov. 11, 2013

(87) PCT Pub. No.: WO2012/156308
PCT Pub. Date: Nov. 22, 2012

(65) Prior Publication Data
US 2014/0094415 A1 Apr. 3, 2014

Related U.S. Application Data

(60) Provisional application No. 61/485,898, filed on May 13, 2011.

(30) Foreign Application Priority Data

May 13, 2011 (EP) ..................................... 11165994

(51) Int. Cl.
C07K 7/06 (2006.01)
(52) U.S. Cl.
CPC ........................................ C07K 7/06 (2013.01)
(58) Field of Classification Search
None
See application file for complete search history.

(56) References Cited

U.S. PATENT DOCUMENTS 7,510,824 B2 3/2009 Tymianski

FOREIGN PATENT DOCUMENTS

| WO | 2007140282 A1 | 12/2007 |
| WO | 2008008348 A2 | 1/2008 |
| WO | 2010004003 A2 | 1/2010 |

OTHER PUBLICATIONS

Demmer O., et al., "Introduction of Functional Groups into Peptides Via N-alkylation," Org. Lett., vol. 10 (10):2015-2018 (Apr. 12, 2008).
International Search Report and Written Opinion for International Application No. PCT/EP2012/058762 (Jun. 20, 2012).
International Preliminary Report on Patentability for International Application No. PCT/EP2012/058762 (Nov. 2, 2012).
Bach A., et al., "Cell-Permeable and Plasma-Stable Peptidomimetic Inhibitors of the Postsynaptic Density-95/N-Methyl-D-Aspartate Receptor Interaction," Journal of Medicinal Chemistry, 54:1333-1346, 2011.
Chaplan S.R., et al., "Quantitative Assessment of Tactile Allodynia in the Rat Paw," Journal of Neuroscience Methods, 53:55-63, 1994.
Egholm M., et al., "PNA Hybridizes to Complementary Oligonucleotides Obeying the Watson-Crick Hydrogen-Bonding Rules," Nature, 365:566-568, 1993.
Hammond M., et al., "Beta Strand Peptidomimetics Brief Communication as Potent PDZ Domain Ligands," Chemistry & Biology, 13:1247-1251, 2006.
Nikolovska-Coleska Z., et al., "Development and Optimization of a Binding Assay for the XIAP BIR3 Domain Using Fluorescence Polarization," Anal. Biochem., 332:261-273, 2004.
Singh S., et al., "LNA (Locked Nucleic Acids): Synthesis and High-Affinity Nucleic Acid Recognition," Chem. Commun., 455-456, 1998.
Wang W., et al., "Creating Conformational Entropy by Increasing Interdomain Mobility in Ligand Binding Regulation: A Revisit to N-Terminal Tandem PDZ Domains of PSD-95," J. Am. Chem. Soc., 131:787-796, 2009.
Hervé F., et al., "CNS Delivery Via Adsorptive Transcytosis," *The AAPS Journal*, vol. 10, No. 3, Sep. 2008, pp. 455-472.
Spatola A.F., "Peptide Backbone Modifications: A Structure-Activity Analysis of Peptides Containing Amide Bond Surrogaes, Conformational Constraints, and Rela," *Chemistry & Biochemistry of Amino Acids, Peptides, and Proteins*, Edited by Boris Weinstein, vol. 7, Chapter 5, 1983, pp. 267-357.
Eildal, J.N.N. et al., "Rigidified Clicked Dimeric Ligands for Studying the Dynamics of the PDZ1-2 Supramodule of PSD-95," *ChemBioChem* 2015, 16, 64-69.
Nissen, K.B. et al. "Design, Synthesis, and Characterization of Fatty Acid Derivatives of a Dimeric Peptide-Based Postsynaptic Density-95 (PSD-95) Inhibitor," *J. Med. Chem.* 2015, 58, 1575-1580.
Nissen, K.B. et al., "Targeting Protein-Protein Interactions with Trimeric Ligands: High Affinity Inhibitors of the MAGUK Protein Family," *PLoS ONE* 10(2): pp. 1-17, Feb. 6, 2015.

*Primary Examiner* — John Ulm
(74) *Attorney, Agent, or Firm* — Gifford, Krass, Sprinkle, Anderson & Citkowski, P.C.

(57) ABSTRACT

The invention provides novel potent inhibitors of the ternary protein complex of nNOS, PSD-95, and the NMDA receptor and pharmaceutical compositions comprising the inhibitors for prophylaxis and/or treatment of excitotoxic-related disease and chronic pain conditions in a subject. The inhibitors are dimeric PSD-95 inhibitors comprising a first peptide or peptide analogue linked to a second peptide or peptide analogue by a linker, wherein the first and the second peptide or peptide analogue comprise at least four amide-bonded residues having a sequence YTXV (SEQ ID NO: 5) or YSXV (SEQ ID NO: 6), wherein a. Y is selected from among E, Q, and A, or an analogue thereof, and b. X is selected from among A, Q, D, N, N-Me-A, N-Me-Q, N-Me-D, and N-Me-N or an analogue thereof, and wherein a Cell Penetrating Peptide (CPP) is linked to the linker or to an amino acid side chain of the first and second peptide or peptide analogue. The linker can be a PEG or NPEG linker.

14 Claims, 23 Drawing Sheets

Scheme 1

A. Ns-NPEG4-diacid-linkerA:

B. Ns-NPEG4-diacid-linkerB:

C. Ns-NPEG4-diacid-linkerC:

HIGH-AFFINITY, DIMERIC INHIBITORS OF PSD-95 AS EFFICIENT NEUROPROTECTANTS AGAINST ISCHEMIC BRAIN DAMAGE AND FOR TREATMENT OF PAIN

FIELD OF THE INVENTION

The scaffolding protein PSD-95 is a potential target for treatment of ischemic stroke and traumatic brain injury as well as for chronic pain conditions, such as neuropathic and inflammatory pain. The present invention is directed to the provision of dimeric peptide analogues acting as inhibitors of PSD-95-related protein-protein interactions.

BACKGROUND OF THE INVENTION

Protein-protein interactions (PPIs) are essential to vital cellular processes, and are involved in numerous patophysiological states, where they serve as potential targets for therapeutic intervention. PPIs have generally been perceived as difficult to target with therapeutic molecules, since they are often characterized by large, flat, and hydrophobic interfaces.

A class of PPIs is one involving PDZ domains [PDZ is an abbreviation for postsynaptic density protein-95 (PSD-95), *Drosophila* homologue discs large tumor suppressor (DlgA) and zonula occludens-1 protein (ZO-1)]. PDZ domains often function as modules in scaffolding proteins that are involved in assembling large protein complexes in the cell, and are highly abundant in eukaryotic organisms. PDZ domains comprise about 90 amino acids and generally interact with the C-terminal of the interacting protein. PSD-95, contains three PDZ domains, PDZ1-3, which bind peptide ligands with the consensus sequence Glu/Gln-Ser/Thr-X-Val-COOH.

The structural basis for the interaction of PDZ domains with C-terminal peptides was first elucidated by an X-ray crystallographic structure of PDZ3 of PSD-95 complexed with a native peptide ligand, CRIPT (Sequence: YKQTSV (SEQ ID NO: 3)). PDZ3 contains six antiparallel β-strands (βA-βF) and two α-helices (αA and αB), and the C-terminal peptide ligand binds as an additional anti-parallel β-strand into a groove between the βB strand and αB helix. Two residues in the peptide ligand are considered particularly important for affinity and specificity, the first ($P^0$) and the third ($P^{-2}$) amino acids (counting from the C-terminal). The side chain of the amino acid in $P^0$ position projects into a hydrophobic pocket and an amino acid with an aliphatic side chains (Val, Ile and Leu) is required. In the PDZ3-CRIPT structure, the hydroxyloxygen of Thr ($P^{-2}$) forms a hydrogen bond with the nitrogen of an imidazole side chain of His372. A conserved Gly-Leu-Gly-Phe (SEQ ID NO: 15) (position 322-325 in PDZ3) motif and a positively charged residue (Arg318 in PDZ3) of PDZ domains mediate binding to the C-terminal carboxylate group.

The PDZ1 and PDZ2 domains of PSD-95 interact with several proteins including the simultaneous binding of the N-methyl-D-aspartate (NMDA)-type of ionotropic glutamate receptors and the nitric oxide producing enzyme, neuronal nitric oxide synthase (nNOS) (FIG. 1). NMDA receptors are the principal mediators of excitotoxicity, which is implicated in neurodegenerative diseases and acute brain injuries, and although antagonists of the NMDA receptor efficiently reduce excitotoxicity by preventing glutamate-mediated ion-flux, they also prevent physiological important processes. Thus NMDA receptor antagonists have failed in clinical trials for stroke due to low tolerance and lack of efficacy. Instead, specific inhibition of excitotoxicity can be obtained by perturbing the intracellular nNOS/PSD-95/NMDA receptor complex with PSD-95 inhibitors (FIG. 1). PSD-95 simultaneously binds the NMDA receptor, primarily GluN2A and GluN2B subunits, and nNOS via PDZ1 and PDZ2. Activation of the NMDA receptor causes influx of calcium ions, which activates nNOS thereby leading to nitric oxide (NO) generation. Thus, PSD-95 mediates a specific association between NMDA receptor activation and NO production, which can be detrimental for the cells if sustained for a longer period, and is a key facilitator of glutamate-mediated neurotoxicity (FIG. 1). Inhibition of the ternary complex of nNOS/PSD-95/NMDA receptor interaction by targeting PSD-95 is known to prevent ischemic brain damage in mice, by impairing the functional link between calcium ion entry and NO production, while the physiological function, such as ion-flux and pro-survival signaling pathways, of the NMDA receptor remains intact.

Inhibition of the nNOS/PSD-95/NMDA receptor complex has previously been achieved with a nonapeptide, corresponding to the C-terminal of GluN2B, fused to HIV-1 Tat peptide, known for its ability to facilitate membrane and blood-brain barrier permeability. This 20-mer peptide (Tat-NR2B9c; Sequence: YGRKKRRQRRRKLSSIESDV (SEQ ID NO: 4)) has shown promising neuroprotective properties in rat models of ischemic brain damage (Aarts et al., Science 298, 2002, p. 846-850, 2002; Sun et al., Stroke 39, 2008, p. 2544-2553) and is currently in clinical trials as a potential drug for the treatment of cerebrovascular ischemia, as seen in stroke. However, this compound suffers from low affinity ($K_i$=4.6 μM; see later) to PDZ1-2 of PSD-95, which potentially makes it an inefficient and non-selective compound.

WO2010/004003 describes dimeric peptide ligands linked by a polyethylene glycol linker (PEG) that simultaneously bind to the PDZ1 and PDZ2 domains of PSD-95 and their use for treatment of cerebrovascular ischemia. There remains a need for PSD-95 inhibitors with a higher affinity for PDZ1 and PDZ2 domains, and that have an improved therapeutic effect in vivo for the treatment of treatment of ischemic stroke and traumatic brain injury.

Neuropathic pain is caused by damage to the peripheral or central nervous system due to traumatic injury, surgery, or diseases such as diabetes or autoimmune disorders. Such damage leads to an acute phase response characterized by 'nociceptive pain' and inflammation. In a large proportion of patients, pain persists despite injury healing, resulting in a state of chronic neuropathic pain. In addition to the involvement of inflammation after nerve injury, chronic pain may also be initiated by inflammation induced by mediators released by immune cells, which cause a sensitization of pain pathways. Sensitization of spinal sensory neurons ('wind-up') is a shared feature of neuropathic pain and chronic inflammatory pain, and is evoked by a prolonged activation of nociceptors. The symptoms present as spontaneous burning pain, an exaggerated response to painful stimuli (hyperalgesia), and pain in response to normally non-painful stimuli (allodynia). Chronic pain, particularly as a result of nerve injury, is poorly managed by current drugs such as opioids and non-steroidal anti-inflammatory drugs (NSAIDs). NMDA receptor antagonists block sensitization of pain responses and display good analgesic properties in animal models and clinical settings, but they are associated with unacceptable side-effects and can therefore not be used clinically. Accordingly there is a need for alternative drugs capable of providing improved pain treatments, particularly NMDA receptor related pain symptoms, while avoiding the unacceptable side-effects of current drugs.

SUMMARY OF THE INVENTION

A first embodiment of the present invention provides a compound comprising a first peptide or peptide analogue linked to a second peptide or peptide analogue by a linker, wherein the first and the second peptide or peptide analogue comprise at least four amide-bonded residues having a sequence YTXV (SEQ ID NO: 5) or YSXV (SEQ ID NO: 6), wherein
a. Y is selected from among E, Q, and A, or an analogue thereof, and
b. X is selected from among A, Q, D, N, N-Me-A, N-Me-Q, N-Me-D, and N-Me-N or an analogue thereof, and
wherein a third peptide having the function of a Cell Penetrating Peptide (CPP) is linked to the linker, wherein the third peptide comprises at least 4 amino acid residues selected from arginine and/or lysine. Preferably the linker comprises PEG, wherein at least one oxygen atom of the PEG is substituted with a nitrogen atom to give NPEG, and preferably the third peptide is linked to the nitrogen atom of the NPEG linker, preferably by an amide bond, A second embodiment of the invention provides a compound comprising a first peptide or peptide analogue linked to a second peptide or peptide analogue by a linker, wherein the linker comprises PEG and wherein the first and the second peptide or peptide analogue comprise at least four amide-bonded residues having a sequence YTXV (SEQ ID NO: 5) or YSXV SEQ ID NO: 6), wherein
a. Y is selected from among E, Q, and A, or an analogue thereof, and
b. X is selected from among A, Q, D, N,N-Me-A, N-Me-Q, N-Me-D, and N-Me-N or an analogue thereof, characterised in that a third peptide is linked to a side chain of one of the residues of the first and second peptide or peptide analogue, wherein the third peptide comprises at least 4 amino acid residues selected from arginine and/or lysine and has the function of a Cell Penetrating Peptide (CPP).

In a further embodiment of the above compounds of the invention, the linker is a PEG linker comprising 1-28 ethylene glycol moieties (N=1-28), preferably 4 to 12 ethylene glycol moieties (N=4-12), more preferably 4 to 6 ethylene glycol moieties (N=4-6). In a further embodiment of the compound of the invention, the linker is a PEG-diacid or an NPEG-diacid, and wherein each carboxyl group of the linker is linked to the terminal amino group of a terminal residue of the first or the second peptide or peptide analogue via an amide bond.

In a further embodiment of the above compounds of the invention, the third peptide (CPP) comprises a retroinverso peptide. In a further embodiment of the above compounds of the invention, the third peptide (CPP) is Tat peptide (YGRKKRRQRRR (SEQ ID NO: 7)) or Retroinverso-D-Tat peptide (rrrqrrkkr (SEQ ID NO: 8)).

In a further embodiment of the above compounds of the invention, the peptide or peptide analogue is from 5 to 10 amide-bonded residues in length. In a further embodiment of the above compounds of the invention, the peptide is comprised of at least 4 L-amino acid residues. In a further embodiment of the above compounds of the invention, X is selected from among A, Q, and D. In a further embodiment of the above compounds of the invention, the peptide or peptide analogue is N-alkylated.

The present invention further provides a linker compound comprising a PEG-diacid, wherein one oxygen atom of the PEG is substituted with a nitrogen atom to give NPEG-diacid. In a further embodiment of the linker compound of the invention, the nitrogen atom is linked to a protecting group.

The present invention further provides a pharmaceutical composition comprising a compound according to any one the above embodiments of the invention for use as a medicament. In a further embodiment, the pharmaceutical composition comprising a compound according to any one of the above embodiments of the invention is for use in the prophylaxis and/or treatment of an excitotoxic-related disease in a subject.

The present invention further provides a pharmaceutical composition comprising a compound according to any one of the above embodiments of the invention for use in the prophylaxis and/or treatment of pain in a subject.

The present invention further includes a method of providing prophylaxis and/or treatment of an excitotoxic-related disease or pain in a subject, comprising administering the above pharmaceutical composition to the subject, wherein said disease may be ischemic or traumatic injury of the CNS.

In a further embodiment, the invention provides a pharmaceutical composition for the prophylaxis and/or treatment of pain in a subject, said composition comprising an active compound, said active compound comprises a first peptide or peptide analogue linked to a second peptide or peptide analogue by a linker, wherein the first and the second peptide or peptide analogue comprise at least four amide-bonded residues having a sequence YTXV (SEQ ID NO: 5) or YSXV (SEQ ID NO: 6), wherein (a) Y is selected from among E, Q, and A, or an analogue thereof, and (b) X is selected from among A, Q, D, N,N-Me-A, N-Me-Q, N-Me-D, and N-Me-N or an analogue thereof. In a further embodiment, the linker in said active compound is a PEG linker or an NPEG linker and comprises 4 to 28 ethylene glycol moieties (N=4-28). In a further embodiment, the carboxyl group of the linker in said active compound is linked to a terminal residue of the first or the second peptide or peptide analogue. In a further embodiment, said active compound is selected from among PEG4 (IETAV)$_2$, (SEQ ID NO: 16), NPEG4(IETAV)$_2$ (SEQ ID NO: 16), PEG6(IESDV)$_2$ (SEQ ID NO: 17), and PEG4(IESDV)$_2$ (SEQ ID NO: 17).

Said active compound may further have a third peptide comprising at least 4 amino acid residues selected from arginine and/or lysine and having the function of a CPP, wherein the third peptide is linked to the linker or is linked to a side chain of an amino acid of the first and second peptide or peptide analogue.

BRIEF DESCRIPTION OF THE DRAWINGS

FIG. 6. $^1H$-$^{15}N$ correlation spectra (NMR) of free AB140 (Contours: I1, E2, T3, A4, V5) and AB140 in complex with PDZ1-2 from PSD-95 (remaining a/b contours). The assignments are shown in the spectrum. For the bound form of the dipeptide no attempts have been made to determine which PDZ domain the 'a' peaks and 'b' peaks, respectively, bind to.

DETAILED DESCRIPTION OF THE INVENTION

Figure 1:
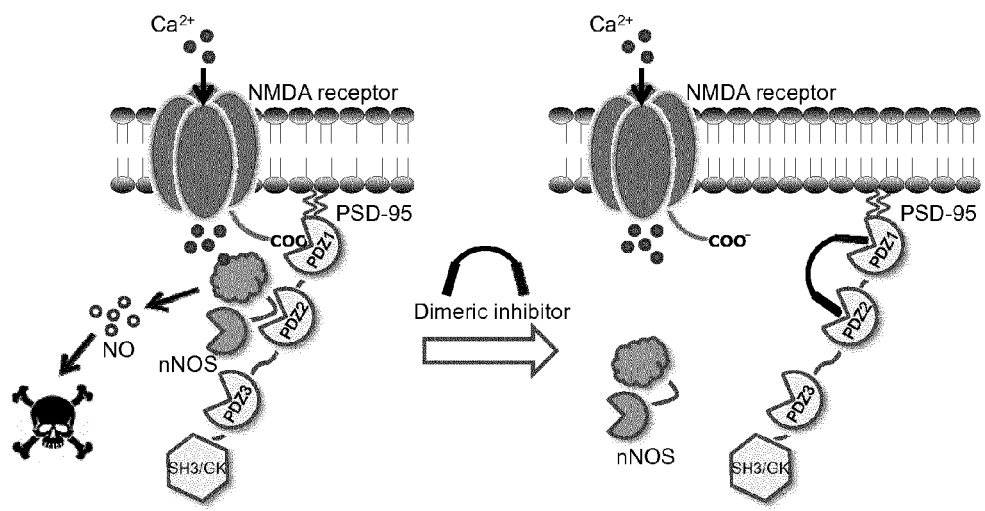
FIG. 1. PSD-95 simultaneously binds the NMDA receptor and nNOS via its PDZ1 and PDZ2 domains. Thereby PSD-95 facilitates the functional link between NMDA receptor activation and NO production, as calcium (Ca$^2$) entry from the NMDA receptor activates nNOS. PSD-95 inhibitors, such as the illustrated dimeric ligand that targets PDZ1-2 of PSD-95, inhibit the formation of the ternary nNOS/PSD-95/NMDA receptor complex and uncouple the link between NMDA receptor activity and NO production, whereby neuroprotection against excitotoxicity is achieved.

I. Definition of Abbreviations and Terms:

"A" or "a" as used herein, can mean one or more, depending on the context in which it is used.

Amide bond is formed by a reaction between a carboxylic acid and an amine (and concomitant elimination of water). Where the reaction is between two amino acid residues, the bond formed as a result of the reaction is known as a peptide linkage (peptide bond);

Amino acids, that are proteogenic are named herein using either its 1-letter or 3-letter code according to the recommendations from IUPAC, see for example http://www.chem.qmw.ac.uk/iupac. If nothing else is specified an amino acid may be of D or L-form. In the description (but not in the sequence listing) a 3-letter code starting with a capital letter indicates an amino acid of L-form, whereas a 3-letter code in small letters indicates an amino acid of D-form;

"comprising" should be understood in an inclusive manner. Hence, by way of example, a composition comprising compound X, may comprise compound X and optionally additional compounds;

CFA, Complete Freunds Adjuvant;

CNS, central nervous sytem;

CPP, cell penetrating peptide; characterised by the ability to cross the plasma membrane of mammalian cells, and thereby may give rise to the intracellular delivery of cargo molecules, such as peptides, proteins, oligonucleotides to which it is linked;

DCM, Dichloromethane;

Dimeric PSD-95 inhibitor, is a PSD-95 inhibitor comprising two peptide or peptide analogues, that are covalently linked by means of a linker, capable of binding to, or interacting with, PDZ1 and PDZ2 of PSD-95 simultaneously, hence;

$P^0$, Defined as the first amino acid residue or analogue corresponding to the C-terminal amino acid of the peptide/peptide analogue;

$P^{-1}$, Defined as the second amino acid residue or analogue thereof counting from the C-terminal amino acid of the peptide/peptide analogue;

$P^{-2}$, Defined as the third amino acid residue or analogue thereof counting from the C-terminal amino acid of the peptide/peptide analogue;

$P^{-3}$, Defined as the fourth amino acid residue or analogue thereof counting from the C-terminal amino acid of the peptide/peptide analogue;

$P^{-4}$, Defined as the fifth amino acid residue or analogue thereof counting from the C-terminal amino acid of the peptide/peptide analogue;

$P^{-5}$, Defined as the sixth amino acid residue or analogue thereof counting from the C-terminal amino acid of the peptide/peptide analogue DIPEA, diisopropylethylamine;

DMF, N,N-Dimethylformamide;

Ethylene glycol moiety, here refers to the structural unit that constitute a PEG or NPEG linker. A more technical name of a 'ethylene glycol moiety' is 'oxyethylene', and the chemical formula of the unit is here shown:

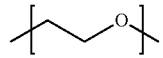

FP, fluorescence polarization;

HATU, O-(7-azabenzotriazol-1-yl)-N,N,N',N'-tetramethyluronium hexafluorophosphate;

HBTU, O-(benzotriazol-1-yl)-N,N,N',N'-tetramethyluronium hexafluorophosphate

Mammalian cell, is intended to indicate any cell of mammalian origin. The cell may be an established cell line, many of which are available from The American Type Culture Collection (ATCC, Virginia, USA) or a primary cell with a limited life span derived from a mammalian tissue, including tissues derived from a transgenic animal, or a newly established immortal cell line derived from a mammalian tissue including transgenic tissues, or a hybrid cell or cell line derived by fusing different cell types of mammalian origin e.g. hybridoma cell lines. The cells may optionally express one or more non-native gene products, e.g. receptors;

MCAO, middle cerebral artery occlusion;

nNOS, neuronal nitric oxide synthase;

NO, nitric oxide;

NMDA, N-methyl-D-aspartate;

NMR, nuclear magnetic resonance;

NPEG, is the novel linker type described herein, which is derived from the classical PEG linker, but where one or more of the backbone oxygen atoms is replaced with a nitrogen atom;

Ns, ortho-nitrobenzenesulfonyl (sometimes abbreviated oNBS);

PDZ, Postsynaptic density protein-95 (PSD-95), *Drosophila* homologue discs large tumor suppressor (DlgA), Zonula occludens-1 protein (zo-1);

PEG, polyethylene glycol; PEG is a polymer of ethylene glycol having the chemical formula $C_{2n+2}H_{4n+6}O_{n+2}$, and the repeating structure:

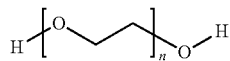

where for example 12 PEG moieties, or PEG12, corresponds to a polymer of 12 ethylene glycol moieties (n=12);

PPIs, protein-protein interactions;

PSD-95, postsynaptic density protein-95;

PSD-95 inhibitor, is a compound that binds to PDZ1, PDZ2, or both PDZ1 and PDZ2 of PSD-95 and inhibits the PPIs that are facilitated by these PDZ domains in the cell. An example of an interaction that is inhibited by a PSD-95 inhibitor is the ternary complex of nNOS, PSD-95 and NMDA receptor;

Retroinverso, retroinverso peptides are composed of D-amino acids assembled in the reverse order from that of the parent L-amino acid sequence;

Retroinverso-D-Tat sequence, a 9-mer CPP sequence made by reverting the Tat sequence and using D-amino acids (rrrqrrkkr (SEQ ID NO: 8)), which facilitates permeability across biological membranes, including the blood-brain barrier, and whose structure renders it stable to protease enzymes;

SEM, standard error of mean;

Tat sequence, an 11-mer CPP sequence (YGRKKRRQRRR (SEQ ID NO: 7)) derived from the human immunodeficiency virus-type 1 (HIV-1) Tat protein, which facilitates permeability across biological membranes, including the blood-brain barrier;

TFA, trifluoracetic acid;

THF, tetrahydrofuran;

TIPS, triisopropylsilane;

I. Chemical Structure of CPP-containing Dimeric PSD-95 Inhibitors

The invention provides a dimeric PSD-95 inhibitor comprising a first peptide or peptide analogue linked to a second peptide or peptide analogue by a linker, wherein the first and the second peptide or peptide analogue comprise at least four amide-bonded residues having the sequence YTXV (SEQ ID NO: 5) or YSXV (SEQ ID NO: 6), wherein Y is selected from among E, Q, and A, or an analogue of the selected residue, and X is selected from among A, Q, D, N,N-Me-A, N-Me-Q, N-Me-D, and N-Me-N or an analogue of the selected residue. The dimeric PSD-95 inhibitor is further characterized in that a third peptide is linked to the inhibitor, said third peptide being a CPP having cell penetrating properties.

I.i The Linker of the Dimeric PSD-95 Inhibitor

The first and second peptide or peptide analogues of the dimeric PSD-95 inhibitor are linked together by means of a linker. Suitable linkers include a linker comprising NPEG, polyethylene glycol (PEG); polyamine (Hervé F et al, AAPS J, 2008, p. 455); peptide nucleic acid (PNA) (Egholm et al., 2005 Nature 365, p. 566); locked nucleic acid (LNA) (Singh et al., 1998, Chem. Commun., p. 455); triazoles, piperazines, oximes, thiazolidines, aromatic ring systems, alkanes, alkenes, alkynes, cyclic alkanes, cyclic alkenes, amides, thioamides, ethers, and hydrazones. When the linker is a PEG (or NPEG) linker it may also comprise an active functional group, such as an electrophilic or nucleophilic functional group (WO/2007/140282), which can be used to attach the PEG linker to each peptide (or peptide analogue) inhibitor. Suitable functional groups for attachment include amino-reactive electrophilic groups, selected from among N-hydroxysuccinimide (NHS) ester, p-nitrophenyl ester, succinimidyl carbonate, p-nitrophenyl carbonate, succinimidyl urethane, isocyanate, isothiocyanate, acyl azide, sulfonyl chloride, aldehyde, carbonate, imidioester or anhydride; and thio-reactive groups selected from among maleimide, haloacetyl, alkyl halide derivatives, aziridine, acryloyl derivatives arylating agents or thio-disulfide exchange reagents. Suitable nucleophilic functional groups include amine, hydrazide, carbazate, acyl hydrazide, semicarbamate or hydrazine, which can undergo reactions with aldehyde or carboxyl groups on the peptide or peptide analogue inhibitor.

The optimal length of linker in the dimeric PSD-95 inhibitor will depend on the selected linker. When the linker is PEG, the number of ethylene glycol moieties (n) of PEG may lie between n=1-28 or n=4-28, or the linker may have a length of n=1, 2, 3, 4, 5, 6, 7, 8, 9, 10, 11, or 12. PEG-diacids can be used to link ligands (peptides or peptide analogues), where the e.g. PEG4-linker is modified so that two carboxylic acid groups are present at each end of the linker. Thus, a PEG4-diacid linker prior to the dimerization process is named 4,7,10,13,16-pentaoxanonadecane-1,19-dioic acid. During dimerization of the first and second peptide or peptide analogues of the inhibitor with the linker, the two carboxylic acid groups react with the N-terminal amino groups of the peptides (or peptide analogues) to create amide bonds. The PEG0, 1, 2, 4, 6, 8 and 12 linkers are in accordance with this description.

According to a first embodiment of the dimeric PSD-95 inhibitor, the linker comprises a derivative of a PEG-diacid linker, termed NPEG, wherein one oxygen atom in the backbone of the PEG-diacid linker is replaced with a nitrogen atom. The nitrogen atom may be substituted for any one of oxygen atoms in the backbone of the PEG linker. The carbonyl groups of the NPEG-diacid linker are linked to the first and second peptide or peptide analogue respectively, preferably where the link is an amide bond to a terminal residue of the peptide or peptide analogue.

Figure 2:
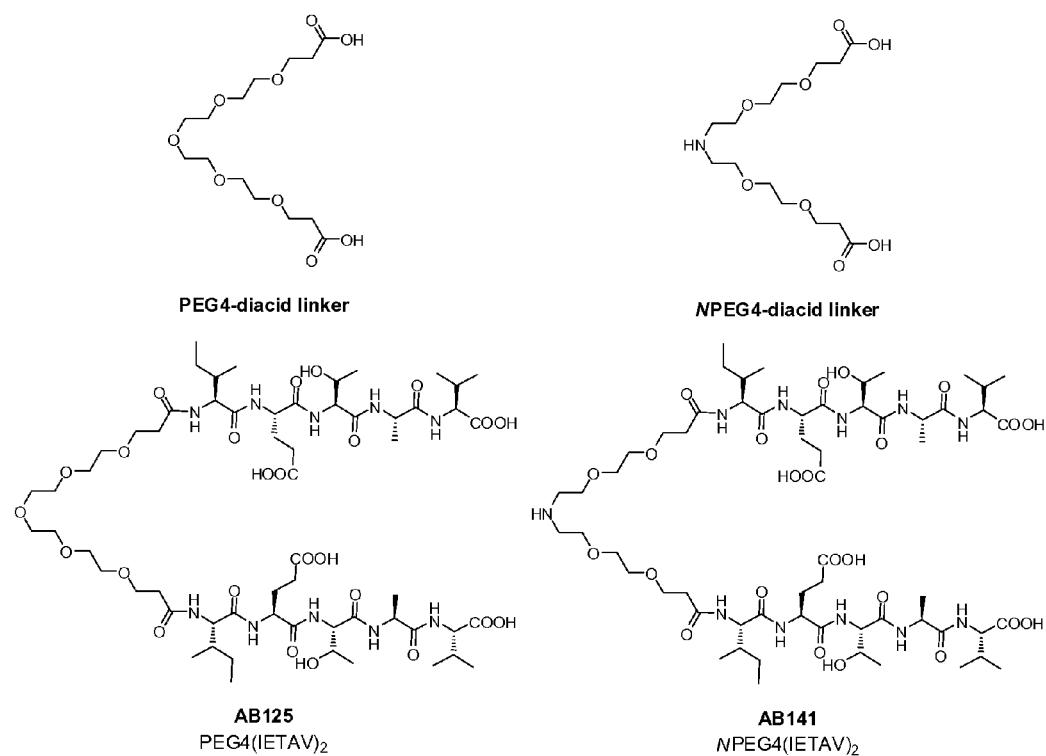
FIG. 2. Chemical structures of PEG4-diacid and NPEG4-diacid linkers, and dimeric compounds AB125 and AB141.
Figure 15:
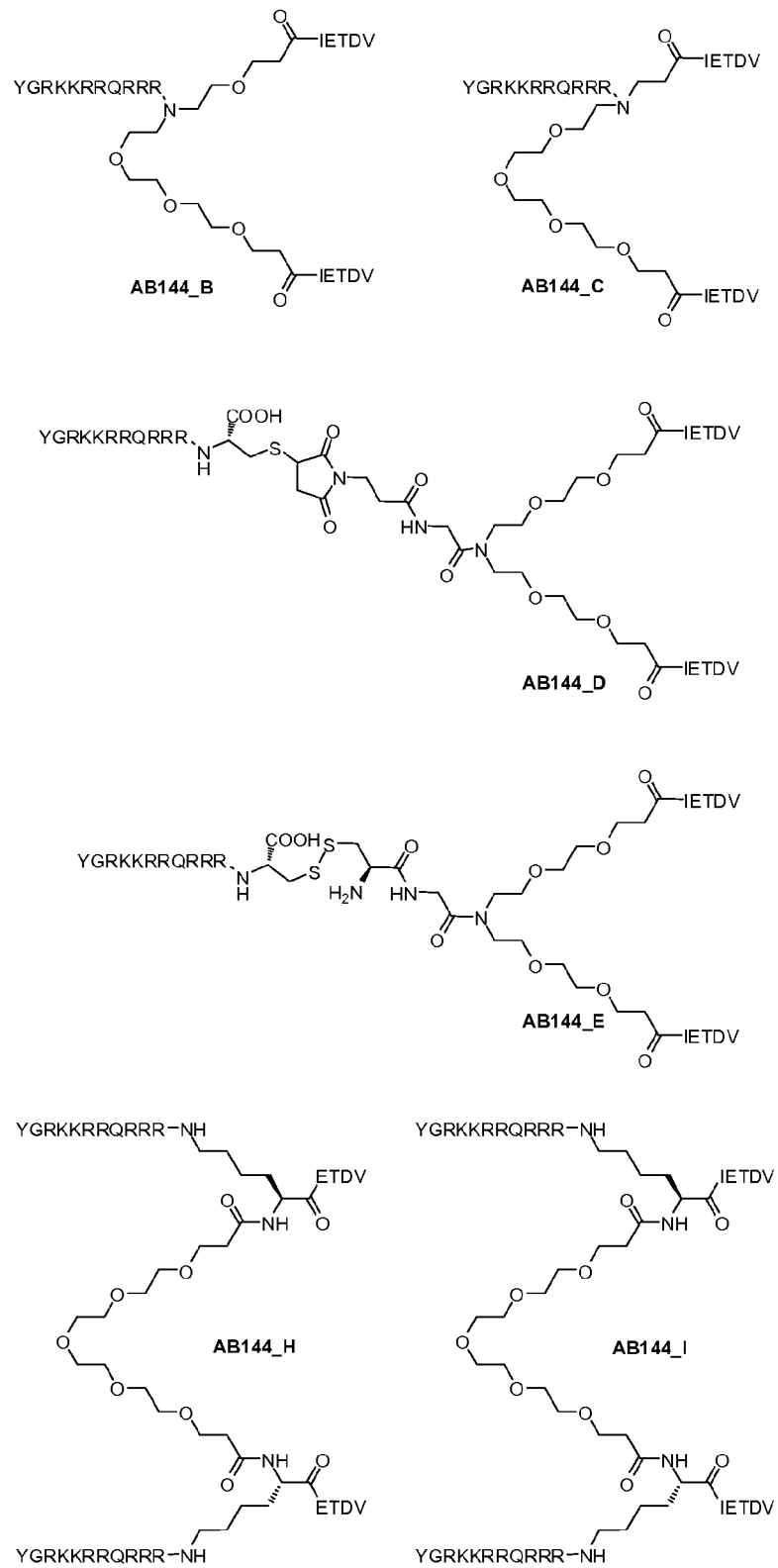
FIG. 15. Chemical structures of AB144 analogues: AB144_B, AB144_C, AB144_D, AB144_E, AB144_H, AB144_I; Same style of structural representation as in FIG. 3 below.

FIG. 2 exemplifies an NPEG linker of the invention, i.e. the NPEG4-diacid linker, where the central oxygen atom is substituted with nitrogen to generate a symmetric NPEG linker, for use in the dimeric inhibitor (e.g. AB141). FIG. 15 exemplifies an NPEG linker in a dimeric inhibitor of the invention where the oxygen atom located in the backbone of the PEG linker, that is substituted with nitrogen, is either one or two 'ethylene glycol moieties' away from the center of the linker, giving an asymmetric NPEG linker (e.g. as in AB144_B and AB144_C).

Figure 3:
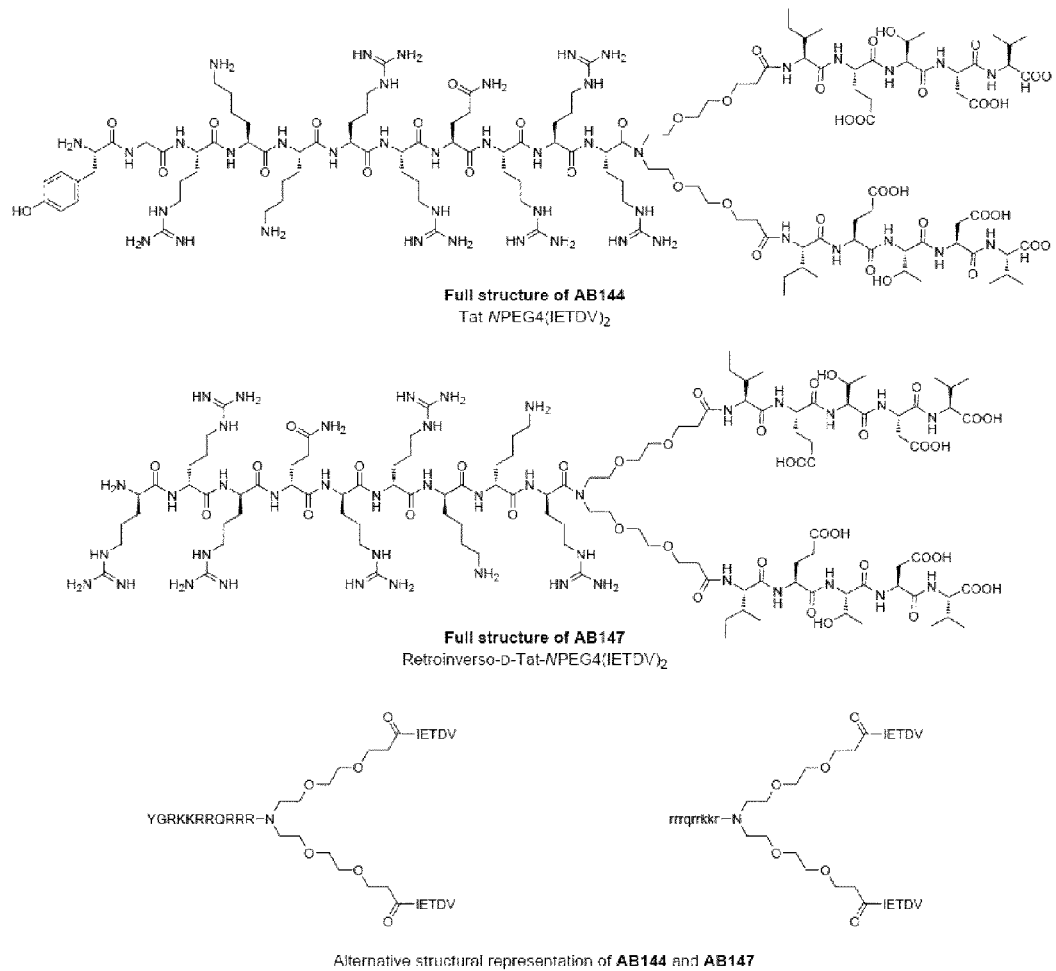
FIG. 3. Chemical structures of dimeric ligands AB144 and AB147, providing both their full structure, and an alternative presentation where the pentapeptide moieties, Tat-sequence and Retroinverse-D-Tat sequence is written in 1-letter amino acid code.

The linker serves two functions. It serves to link the first and second peptide or peptide analogues of the inhibitor, whose function are to act as ligands binding to the PDZ1-2 of PSD-95. The affinity of the peptides/peptide analogues of the inhibitor for the PDZ1-2 of PSD-95 is greatly increased by dimerisation. Additionally, the nitrogen atom in the NPEG linker serves as a chemical 'handle' for further derivatization (FIGS. 2 and 3).

According to a second embodiment of the dimeric PSD-95 inhibitor, the linker comprises PEG-diacid, having a length of from 1 to 28 ethylene glycol moieties (n=1-28), preferably from 1 to 12 ethylene glycol moieties (n=1-12), more preferably from 4 to 6 ethylene glycol moieties (n=4-6). FIG. 2 exemplifies the PEG linker, i.e. the PEG4-diacid linker.

I.ii The Peptide or Peptide Analogue of the Dimeric PSD-95 Inhibitor

According to the first or second embodiment of the dimeric PSD-95 inhibitor, the peptide or peptide analogue is 10, 9, 8, 7 or 6 amide-bonded residues in length, more preferably 5 or 4 amide-bonded residues in length. The peptide or peptide analogue may comprise at least 4 L-amino acid residues. Preferably the residue X in the inhibitor is selected from among A, Q, and D. Suitable analogues of residue Y or X, or analogues of any of the 4 amide-linked residues (YTXV (SEQ ID NO: 5) or YSXV (SEQ ID NO: 6)), or analogues of their amide bonds connecting them, include: D-amino acids, peptoid amino acids, β-amino acids, olefinic double bonds (E-vinyl), retroamides, α-azapeptides, thioesters, esters (depsipeptides), carba replacement of carbonyl (methylamines), methylthio groups, alkanes, ketomethylenes, hydroxyethylenes, hydroxyethylamines, hydroxyethylureas, vinyl fluorides (Chemistry & Biochemistry of amino acids, peptides, and proteins", vol 7, 1983, Boris Weinstein, Ch. 5 by Arno F. Spatola); thioamides (Bach et al., J. Med. Chem., 2011, p. 1333); the aza-@-unit (5-dihydro-2(3H) -pyrazone moiety), particularly position $P^{-1}$ or $P^{-3}$ corresponding to residue X or Y (Hammond et al, Chem. Biol., 2006, p. 1247); where the choice of analogue may be assisted by use of the tools and assays for a peptidomimetic approach as described herein. Additionally, a residue of the first and/or second peptide or peptide analogue of the dimeric PSD-95 inhibitor can be N-alkylated, wherein the N-alkylated residue is at position $P^{-3}$ corresponding to residue Y (WO2010/004003). The N-alkyl group may be selected from among N-methyl, N-ethyl, N-propyl, N-butyl, and N-benzyl. A particularly suitable N-alkyl group may be selected from among N-cyclohexylmethyl, N-cyclohexylethyl, N-phenylethyl, N-phenylpropyl, N-(3,4-dichlorophenyl)propyl, N-(3,4-difluorophenyl)propyl, N-(naphtalene-2-yl)ethyl.

FIG. 2 exemplifies a dimeric PSD-95 inhibitor having a linker according to the first or second embodiment of the invention, comprising a dimerized pentapeptide IETAV (SEQ ID NO: 16) and either a PEG linker, as in PEG4(IETAV)$_2$ (SEQ ID NO: 16) (AB125) or an NPEG linker, as in NPEG4 (IETAV)$_2$ (SEQ ID NO: 16) (AB141).

I.iii The CPP Peptide of the Dimeric PSD-95 Inhibitor

The dimeric PSD-95 inhibitor, according to the first or second embodiment, further comprises a third peptide that has the properties of a CPP. This third CPP peptide comprises at least 4 D-or L amino acid residues, but may be 5, 6, 7, 8, 9, 10 or more D-or L amino acid residues in length. A preferred CPP has an polycationic structure and comprises at least 4 lysine residues, or at least 4 arginine residues, or at least 4 residues comprising both lysine and arginine residues (e.g. Tat peptide; polyarginine peptides, such as 8 arginines; SynB1: RGGRLSYSRRRFSTSTGRA (SEQ ID NO: 9)), or at least 4 amino acids having cationic or basic side chains that are analogues to arginine or lysine, such as for example 5-hydroxylysine, ornithine, 2-amino-3 (or-4) -guanidinopropionic acid, and homoarginine. An alternative CPP has an amphipathic structure and comprises an alternating pattern of polar/charged amino acids and non-polar, hydrophobic amino acids (e.g. penetratin: RQIKIWFQNRRMKWFF (SEQ ID NO: 10); retroinverso-penetratin: kkwkmrrnqfwvrvqr (SEQ ID NO: 11); amphipathic model peptide: KLALKLALKLAKAALKA (SEQ ID NO: 12)).

FIG. 3 exemplifies a dimeric inhibitor having a linker according to the second embodiment of the invention, comprising a dimerized pentapeptide IETDV (SEQ ID NO: 18), an NPEG linker, and a CPP peptide. The CPP is either Tat (Sequence: YGRKKRRQRRR (SEQ ID NO: 7); 1-letter amino acid code), as in Tat-NPEG4(IETDV)$_2$ (SEQ ID NO: 18) (AB144), or Retroinverso-D-Tat (Sequence: rrrqrrkkr (SEQ ID NO: 8); 1-letter D-amino acid code), as in Retroinverso-D-Tat-NPEG4(IETDV)$_2$ (SEQ ID NO: 18) (AB147).

I.iv Linkage of the CPP Peptide to the Dimeric PSD-95 Inhibitor

The dimeric PSD-95 inhibitor, according to the first embodiment comprises a CPP that is linked to the inhibitor via a chemical bond either directly or indirectly to the nitrogen atom in the backbone of the NPEG linker, where the nitrogen atom can be symmetrically- or asymmetrically-positioned in the linker. Linkage of the CPP to the nitrogen of the NPEG linker may be mediated via an amide bond, a maleimide coupling, a disulfide bond, or amino-reactive electrophilic groups, selected from among N-hydroxysuccinimide (NHS) ester, p-nitrophenyl ester, succinimidyl carbonate, p-nitrophenyl carbonate, succinimidyl urethane, isocyanate, isothiocyanate, acyl azide, sulfonyl chloride, aldehyde, carbonate, imidioester or anhydride; and thio-reactive groups selected from among haloacetyl, alkyl halide derivatives, aziridine, acryloyl derivatives arylating agents.

Alternatively, linkage of the CPP to the nitrogen of the linker may be mediated via a spacer group, where a suitable spacer group can for example be any amino acid such as cysteine, glycine, alanine; short alkane chains or short PEG/NPEG chains.

FIGS. 3 and 15 exemplify dimeric inhibitors comprising a dimerized pentapeptide IETDV (SEQ ID NO: 18), an NPEG linker, and a CPP. The CPP can be linked by an amide bond to a symmetric NPEG linker, as in AB144 and AB147; or it can be linked by an amide bond to an asymmetric NPEG linker, as in AB144_B and AB144_C. Alternatively, a CPP comprising a C-terminal Cys can be linked via a maleimide coupling to a maleimide group extending from the NPEG nitrogen atom, as in AB144_D. Alternatively, a CPP comprising a C-terminal Cys can be linked via a disulfide (S—S) bond to a sulfhydryl group extending from the NPEG nitrogen atom, as in AB144_E.

The dimeric PSD-95 inhibitor, according to the second embodiment, comprises a PEG linker, and the CPP that is linked to a side chain of either the first of second peptide or peptide analogue. The CPP may be linked to a side chain of a residue (e.g. an amino acid) in the $P^{-1}$ position of either the first of second peptide or peptide analogue. Preferably the CPP is attached to the side chain of a $>P^{-4}$, or more preferably a $P^{-5}$ or $P^{-6}$ residue (e.g. amino acid) of a first or second peptide or peptide analogue. Linkage of the CPP to the side chain of the residue may be mediated via an amide bond, a maleimide coupling, a disulfide bond, or amino-reactive electrophilic groups, selected from among N-hydroxysuccinimide (NHS) ester, p-nitrophenyl ester, succinimidyl carbonate, p-nitrophenyl carbonate, succinimidyl urethane, isocyanate, isothiocyanate, acyl azide, sulfonyl chloride, aldehyde, carbonate, imidioester or anhydride; and thio-reactive groups selected from among haloacetyl, alkyl halide derivatives, aziridine, acryloyl derivatives arylating agents.

FIG. 15 exemplify dimeric inhibitors comprising a dimerized pentapeptide KETDV (SEQ ID NO: 19), a PEG linker, and a CPP linked to a $P^{-4}$ amino acid (lysine) of a first peptide (pentapeptide), as in AB144_H. In AB144_I the CPP is attached to the side chain of the $P^{-5}$ amino acid of a first peptide (KIETDV (SEQ ID NO: 20), hexapeptide).

II. Ligand Affinity of CPP-containing Dimeric PSD-95 Inhibitors

Figure 5:
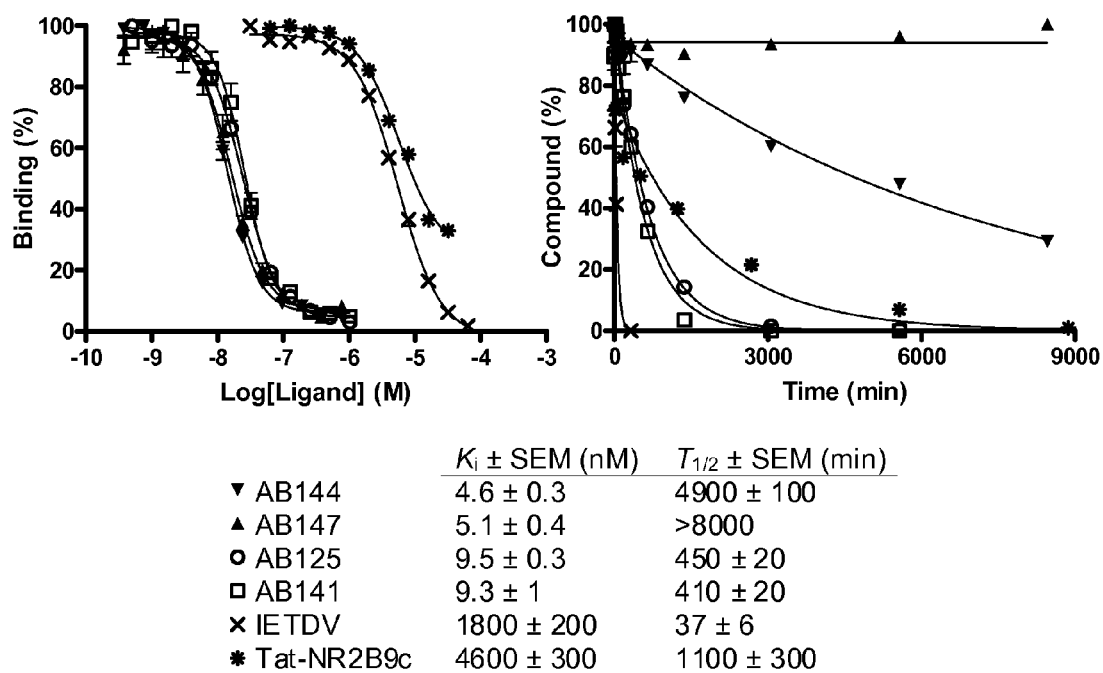
FIG. 5. Affinity towards PDZ1-2 of PSD-95 as measured by fluorescence polarization (left) and stability in human blood plasma in vitro at 37° C. (right). $K_i$ affinity constants and stability half-lives ($T_{1/2}$) are listed in the table. Data in table and fluorescence polarization graph (left) represents ≥3 individual measurements, while representative data from one experiment is shown in the blood plasma graph (right graph).

All of the dimeric PSD-95 inhibitors of the present invention have an affinity for the PDZ1-2 of PSD-95 in the nanomolar range (Example 5), making them highly potent inhibitors (FIG. 5 and Table 2). A CPP, linked to the dimeric PSD-95 inhibitors of the invention, is introduced in order to improve the transport of the inhibitor across the blood brain barrier. Surprisingly, the linkage of a CPP to the dimeric PSD-95 inhibitor also enhances its affinity for the PDZ1-2 of PSD-95. This is exemplified by AB144 and AB147 ($K_i$=4.6±0.3 and 5.1±0.4 nM, respectively), which showed a 2-fold increased affinity over AB141 ($K_i$=9.3±1 nM), and a 1000-fold increased affinity relative to the monomeric Tat-NR2B9c peptide ($K_i$=4600±300 nM). The affinity of the dimeric PSD-95 inhibitor for the PDZ1-2 of PSD-95 is a critical factor in reducing the threshold concentration of drug needed to attain a therapeutic effect, which is particularly important when the drug must cross the blood brain barrier (BBB) to reach its target, since the BBB will tend to limit the accumulation of drug concentration at the target. Surprisingly, a comparison of the dimeric PSD-95 inhibitors reveals that the position and type of coupling of the CPP to the dimeric PSD-95 inhibitor is a key determinant in obtaining the highest degree of affinity for PDZ1-2 of PSD-95. Thus linkage of the CPP via an amide bond to a nitrogen atom of a NPEG substituent of the PEG linker enhances the affinity for PDZ1-2 of PSD-95 two fold over other forms of linkage to the NPEG substituent of the PEG linker, such as disulfide bond linkage or maleimide coupling. Furthermore, amide bond linkage of the CPP to a nitrogen atom of a NPEG substituent of the PEG linker also enhances the affinity for PDZ1-2 of PSD-95 more than two fold overamide bond linkage of the CPP to the first or second peptide.

The dimeric PSD-95 inhibitors of the present invention bind PDZ1 and PDZ2 simultaneously, which may account for their high affinity for these domains. NMR studies (Example 7) confirm a 1:1 binding stoichiometry and unambiguously demonstrate that both the first and second peptide of the dimeric PSD-95 inhibitor either bind PDZ1 or PDZ2 in PDZ1-2 in a truly bivalent binding mode. N-alkylation at the position $P^{-3}$ of the first or second peptide or peptide analogue of the dimeric PSD-95 inhibitor can be used to further increase the affinity of a peptide or peptide analogue for one or more target PDZ domain, thereby enhancing its ability to prevent PPI interactions occurring with said target.

III. Blood Plasma Stability of CPP-containing Dimeric PSD-95 Inhibitors

The CPP-containing dimeric PSD-95 inhibitors of the present invention show a greatly reduced susceptibility to degradation in human blood plasma. This remarkable improved stability is observed for inhibitors comprising the native Tat CPP, and the Retroinverso-D-Tat CPP, which was effectively non-degradable, illustrating the effect of introducing a protease-stable CPP into the dimeric PSD-95 inhibitor (Example 6).

IV. Blood-Brain Barrier Permeability of CPP-containing Dimeric PSD-95 Inhibitors The CPP-containing dimeric PSD-95 inhibitors of the present invention, despite the relatively large molecular size of these peptide inhibitors, have the ability to cross the blood-brain barrier, which is important for their therapeutic function as a neuroprotectant in the brain of a mammal. This property is exemplified for the CPP-containing dimeric PSD-95 inhibitors, AB144 and AB147 which contain Tat or retroinverso-D-Tat CPP (Example 8).

V. In Vivo Neuroprotective Properties of CPP-containing Dimeric PSD-95 Inhibitors V.i CPP-containing Dimeric PSD-95 Inhibitors Reduce Infarct Volumes in Subjects with Cerebral Focal Ischemia.

The CPP-containing dimeric PSD-95 inhibitors of the present invention, when administered to a subject suffering from cerebral focal ischemia, can significantly reduce ischemic tissue damage. The therapeutic effect of these dimeric PSD-95 inhibitors has been demonstrated in a pMCAO model of cerebral focal ischemia in adult mice, where the inhibitors were intravenously injected after the insult, followed by a 6 hour or 48 hour post-surgical survival period, after which the volume of the infarct was measured (Example 9). The demonstrated efficacy of the CPP-containing dimeric PSD-95 inhibitors as an in vivo neuroprotectant is due to the synergistic effect of their high affinity for their target (nanomolar affinity for PDZ1-2 domain of PSD-95), their blood-brain barrier permeability, and their high in vivo stability.

Control studies confirmed that the therapeutic effect observed on administration of CPP-containing dimeric PSD-95 inhibitors to mice having cerebral focal ischemia is not due to secondary effects due to the manipulation of the mice and their treatment (Example 9).

V.ii CPP-containing Dimeric PSD-95 Inhibitors Improve Motor Function in Subjects with Cerebral Focal Ischemia.

Focal cerebral ischemia induced by pMCAO in mice affects cortical brain areas controlling the contralateral front- and hind-limb including the paws. Administration of CPP-containing dimeric PSD-95 inhibitors of the invention to mice undergoing pMCAO preserves their motor function. The treated mice were seen to maintain their total grip strength (both paws) and, their grip strength analysis showed no asymmetry between the right and left front paw, consistent with a neuroprotective effect. Furthermore, rotarod performance tests showed that treated mice showed improved short term learning skill and the total time spend on the rod was significantly longer (Example 10). These improved motor function and learning skills conferred by treatment with CPP-containing dimeric PSD-95 inhibitors of the invention provide further evidence of the therapeutic value of these drugs.

VI. Tools for Monitoring and Evaluating the Inhibitor Properties of the CPP-containing Dimeric PSD-95 Inhibitors of the Invention VI.i. Fluorescence Polarization (FP) Assay: as described below, Example 1 provides a convenient and reliable way to monitor and evaluate the inhibitor properties of a PSD-95 inhibitor of the invention. The FP assay allows a wide range of peptide analogues to be tested and compared with respect to their interaction with PDZ domains, and their specificity with respect to the tandem PDZ1-2 of PSD-95. PDZ1-2 is expressed using standard recombinant DNA technology known to those skilled in the art. Purification of the expressed PDZ1-2 domain may be facilitated by the inclusion of an affinity tag (e.g. poly-histidine-tag, Glutathione-S-transferase-tag, or antibody-tag such as FLAG-tag) in the expressed protein comprising the PDZ domain (e.g. fusion protein), and the use of an affinity resin to selective purify tagged PDZ domain proteins.

Figure 4:
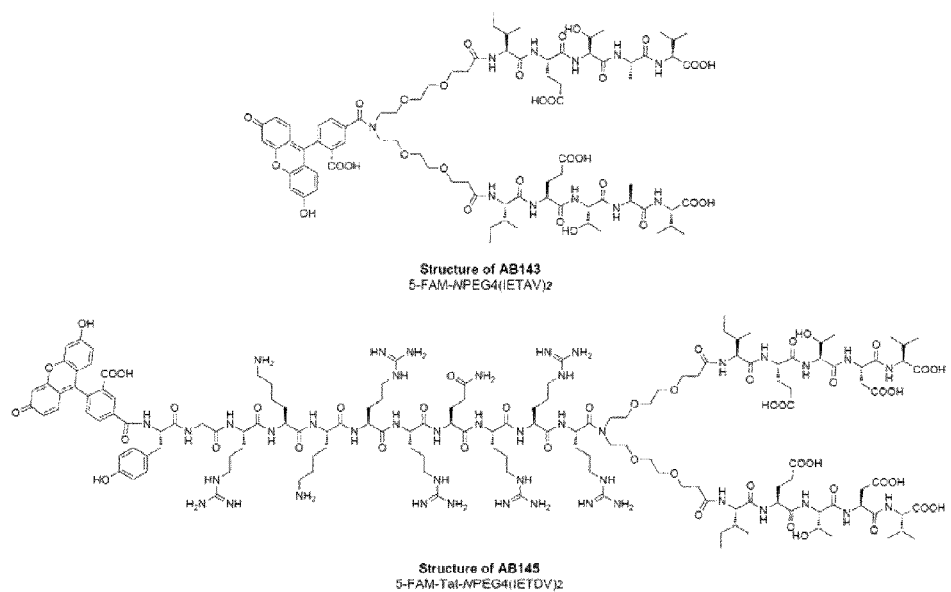
FIG. 4. Chemical structure of the fluorescent dimeric ligand, AB143 and AB145, which are used as probes in the fluorescence polarization assay, and/or used to study CNS permeability.

More specifically, the assay is based on a heterologous competition binding assay, where the affinity measured as $IC_{50}$ of a given (non-fluorescent) peptide analogue for a PDZ domain is measured in the presence of a fixed concentration of a fluorescent labeled dimeric ligand (AB143; FIG. 4). Determined $IC_{50}$ values are converted to $K_i$ values (Nikolovska-Coleska et al, Anal. Biochem. 2004, 332, p. 261-273). The 5-FAM fluorophore may be attached to the dimeric ligand by coupling with HATU or HBTU. AB143 is a high-affinity probe ($K_d$=7.8 nM), thereby allowing precise $K_i$ measurements of un-labeled ligands with affinities in the same range (low nanomolar affinities).

VI.ii. Blood-brain Barrier Permeability. Fluorescent-labeled to permeate the blood-brain barrier, and thereby to enter the brain. After injection of the compounds, the mice are perfused with paraformaldehyde and the brains are carefully removed, post-fixed in paraformaldehyde, processed into coronal sections, and quantified for fluorescence (Example 8).

VI.iii. pMCAO. Experimental stroke i.e. permanent MCA occlusion (pMCAO), intend to provoke a pathological condition similar to that seen in humans, with the primary aim to study basic cellular processes or to develop new therapies for stroke treatment. Studies have shown that direct occlusion of the distal part of the MCA in mice is a highly reproducible technique and associated with low mortality. The MCA is electrocoagulated through a small craniotomy, resulting in a unilateral cortical infarct within lamina I-VI of the frontal and parietal cortices. The infarct volumes obtained following pMCAO is highly reproducible which makes this model well suited for investigating the therapeutic effect of new treatment strategies.

VI.iv. Behavioural Tests. A behavioral test has to be sensitive enough to detect the disabilities of the animals, and give results that can be reproduced and explained from what is known about the condition. The stroke lesion induced by pMCAO on mice affects cortical brain areas controlling the contralateral front- and hind-limb including the paws, so behavior tests (e.g. rotarod and grip test) can be used to determine the motor function of the mice.

VII. Methods for Synthesising and Characterizing CPP-containing Dimeric PSD-95 Inhibitors of the Invention VII.i Peptide Synthesis: Fmoc-based solid-phase peptide synthesis (SPPS) provides a suitable procedure for the synthesis of the PDZ binding peptide moieties and CPPs, whereby a dimeric PSD-95 inhibitor of the invention may be prepared, and for making monomeric control compounds. Peptides with a natural C-terminal amino acid residue, such as Val, may be synthesized starting with pre-loaded Wang resins. In the case of peptides having a C-terminal cysteine, then a 2-chlorotrityl chloride resin may be used, where the residue is loaded on the resin using diisopropylethylamine (DIPEA) (resin/amino acid/DIPEA in 1:3:10) in DCM for 2 hours, then capped with methanol, prior to Fmoc deprotection and coupling of the consecutive amino acid residue. A detailed description of a suitable Fmoc-based SPPS protocol is given below in Example 1. Methods for N-alkylation of peptides is described in WO2010/004003.

VII.ii Synthesis of NPEG Linker: Ns-NPEG4-diacid-linkers are synthesized by solid-phase chemistry as described in Example 1. The present invention provides a linker comprising a PEG-diacid, wherein one oxygen atom in the backbone of the PEG-diacid linker is substituted with a nitrogen atom to give NPEG-diacid. In a further embodiment, the nitrogen atom of the NPEG-diacid is linked to a protecting group. Suitable protecting groups include o-nitrobenzenesulfonyl (Abbreviated: oNBS or Ns), p-nitrobenzenesulfonyl (pNBS), 2,4-Dinitrobenzenesulfonyl (dNBS). Also other N-protecting groups can be used such as α,α-dimethyl-3,5-dimethoxybenzyloxycarbonyl (Ddz), 2-nitrophenylsulfenyl (Nps), 2-(4-biphenyl)isopropoxycarbonyl (Bpoc), triphenylmethyl (trityl, Trt), benzyloxycarbonyl (Z), 9-fluorenylmethoxycarbonyl (Fmoc), 1-(4,4-dimethyl-2,6-dioxocyclohex-1-ylidene)-3-ethyl (Dde), 1-(4,4-dimethyl-2,6-dioxocyclohex-1-ylidene)-3-methylbutyl (ivDde), 2,2,2-trichloroethyloxycarbonyl (Troc), allyloxycarbonyl (Alloc), p-nitrobenzyloxycarbonyl (pNZ), o-nitrobenzyloxycarbonyl (oNZ) and 6-nitroveratryloxycarbonyl (NVOC), azidomethoxycarbonyl (Azoc), tert-butyloxycarbonyl (Boc), 2-trimethylsilylethyl carbamate (Teoc) and 2-chlorobenzyloxycarbonyl (Cl—Z)

The number of ethylene glycol moieties (n) in the PEG and NPEG-diacid may lie between n1-28, or the linker may have a length of n=1, 2, 3, 4, 5, 6, 7, 8, 9, 10, 11, or 12 ethylene glycol moieties.

VII.iii Synthesis of Dimeric Ligands: Dimeric ligands can be produced by activating the Ns-NPEG4-diacid-linkers or PEG4-diacid linker in situ with coupling reagents such as HBTU and HATU, followed by incubation with the N-terminal amino group of the resin-bound peptide ligand. Using this procedure, the dimerization procedure is limited to a one-step reaction.

VII.iv Chemical Analysis: The compounds are analyzed by ESI-LC/MS, analytical HPLC, and high resolution mass spectrometry, employing techniques well-known to the skilled man, and exemplified in Example 1.

VIII. CPP-containing Dimeric PSD-95 Inhibitors According to the First or Second Embodiment of the Invention for Therapeutic Treatment of Excitotoxic-related Disorders Such as Ischemic Stroke or Traumatic Injury In neuronal synapses, the C-termini of NMDA receptor subunits interact with PDZ domains of PSD-95 linking them to downstream neurotoxic signaling molecules (e.g nNOS) leading to NO production and excitotoxicity. The present invention provides inhibitors that can block NMDA receptors and nNOS interacting in a cell, without impairing the NMDA receptor ionic currents and calcium signalling functions of the NMDA receptor. Thus a CPP-containing dimeric PSD-95 inhibitor of the invention acts as a neuroprotectant of one or more cells or tissues providing a specific strategy for treating excitotoxic disorders, including spinal cord injury, stroke, traumatic brain injury, ischemic injury of the central nervous system (CNS), epilepsy, neurodegenerative diseases of the CNS.

Therapeutic treatment of subjects at risk or presently suffering from the above disorders and diseases may be given either prophylactic treatment to reduce the risk of the disorder or disease onset or therapeutic treatment following the disorder or disease onset. The subject may be a mammalian or human patient.

IX. Dimeric PSD-95 Inhibitors for Therapeutic Treatment of Treatment of Pain

It is surprisingly shown that dimeric PSD-95 inhibitors of the present invention are effective in reduction of pain in a subject (mammal or human patient) and furthermore, that these inhibitors can be used in therapeutic treatment since they do not cause any simultaneous deleterious side effects on cognitive and motor function of the subject. The pain, to be treated, may be chronic pain, which may be chronic neuropathic pain or chronic inflammatory pain. The neuropathic pain may be induced by damage to the peripheral or central nervous system as a result of traumatic injury, surgery, or diseases such as diabetes or autoimmune disorders. Where pain persists the condition is chronic neuropathic pain. Chronic inflammatory pain may be induced by inflammation after nerve injury, as well as being initiated by inflammation induced by alien matter, where mediators released by immune cells cause a sensitization of pain pathways, i.e. a 'wind up' of sensory neurons located in the spinal cord. Thus, an effective analgesic drug must be able to reach spinal cord tissue and find its target, in this case PSD-95, in order to have a pain-relieving effect. Thereby, the compounds must be able to pass the blood-brain barrier and/or blood-spinal cord barrier to be able to reach spinal cord tissue. A suitable dimeric PSD-95 inhibitor for treating chronic pain, comprises a first peptide or peptide analogue linked to a second peptide or peptide analogue by a linker, wherein the first and the second peptide or peptide analogue comprise at least four amide-bonded residues having the sequence YTXV (SEQ ID NO: 5) or YSXV (SEQ ID NO: 6), wherein Y is selected from among E, Q, and A, or an analogue of the selected residue, and X is selected from among A, Q, D, N, N-Me-A, N-Me-Q, N-Me-D, and N-Me-N or an analogue of the selected residue. Examples of suitable dimeric PSD-95 inhibitors include AB125, and AB122 having the structure PEG6(IESDV)$_2$ (SEQ ID NO: 17) [corresponding to compound 77 in WO2010/004003] and AB123 having the structure PEG4 (IESDV)$_2$ (SEQ ID NO: 17) [corresponding to compound 78 in WO2010/004003] and AB141 [having an NPEG linker]. These compounds are surprisingly able to reach their target, PSD-95, in the spinal cord (Example 12), despite being hydrophilic and large chemical structures, and despite not being attached to a CPP—as these are properties that normally prevent compounds from passing the blood-brain barrier and/or blood-spinal cord barrier and thus prevent the compounds from entering CNS. Additionally, the inhibitor may further comprise a third peptide, wherein said third peptide is a CPP having cell penetrating properties is linked to the inhibitor, giving an inhibitor of the present invention.

X. In Vivo Analgesic Effects of Dimeric PSD-95 Inhibitors for Therapeutic Treatment of Chronic Pain NMDA receptor antagonism shows anti-nociceptive action in humans and animal models of chronic pain, but is associated with severe disturbances of cognitive and motor function.

The absence of deleterious side-effects of AB125 and AB144 in comparison to the selective NMDA receptor antagonist, MK-801, on mechanical hyperalgesia is demonstrated in the Complete Freund's Adjuvant (CFA) model of chronic inflammatory pain. A reduction in side-effect of dimeric PSD-95 inhibitors, is demonstrated by comparing the effects of AB125 and MK-801 in the social transmission of food preference (STFP) test of long-term memory and the modified Y-maze test of attention, as well as in the rotarod test of motor performance.

Figure 17:
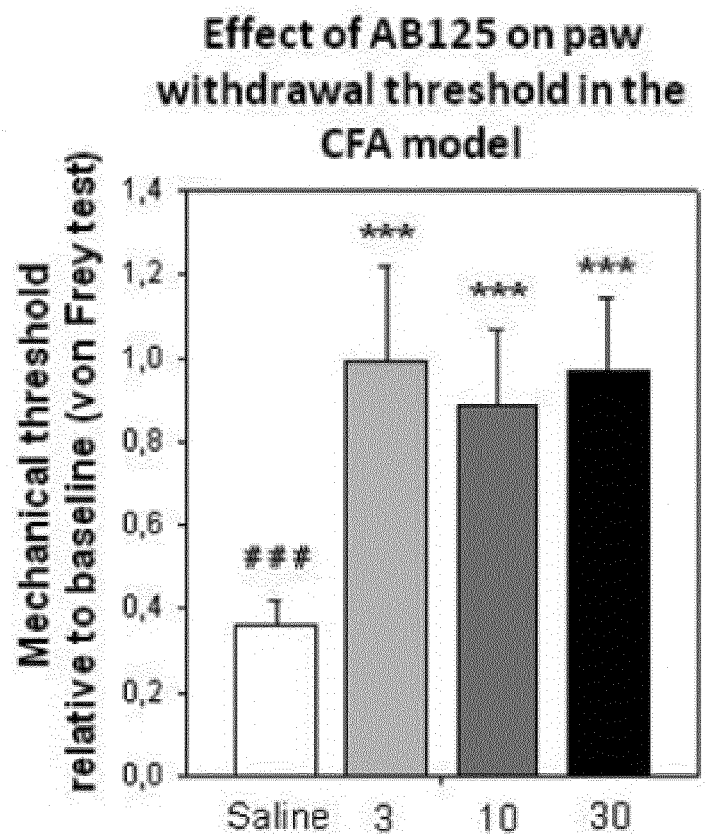
FIG. 17. Effect of AB125 in the complete Freund's adjuvant model of inflammatory pain. Animals were treated with intraplantar CFA and intraperitoneally AB125 (0, 3, 10, or 30 mg/kg), 24 hours before testing. Mechanical hyperalgesia/allodynia was measured with the von Frey method. Data are expressed as mean±SEM, showing the paw withdrawal threshold relative to baseline values (i.e. <1.0 corresponds to hyperalgesia/allodynia). Saline-treated mice showed a marked response to CFA, with mechanical threshold reduced to 36% of baseline (###; p<0.001). This reduction was not observed in mice treated with 3, 10, or 30 mg/kg AB125. Threshold in mice treated with 3, 10 or 30 mg/kg AB125 differed significantly from saline-treated mice (***: p<0.001).
Figure 18:
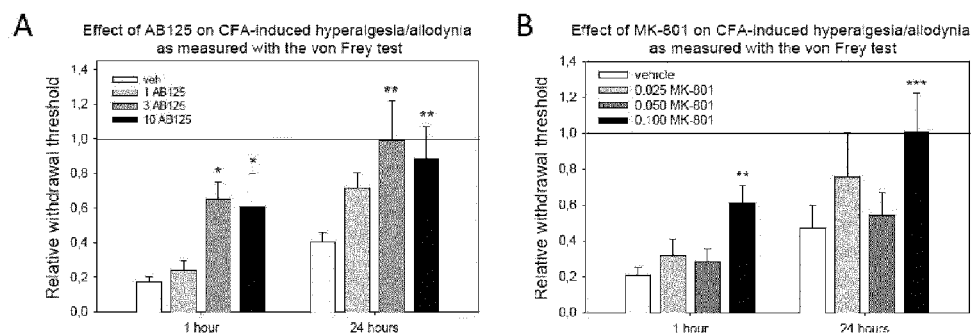
FIG. 18. The effect of AB125 (a) and MK-801 (b) on CFA-induced hyperalgesia when given simultaneously with CFA. For AB125, the ANCOVA revealed a significant main effect of baseline (F1,47=4.61; p=0.037), a significant main effect of treatment (F3,47=5.00; p=0.004), a significant main effect of time (F1,48=42.02; p<0.001), and no significant treatment by time interaction (F3,48=0.71; p=0.552). Planned Comparisons revealed that AB125 significantly reversed the CFA-induced hyperalgesia at 3 mg/kg (p=0.012) and 10 mg/kg (p=0.03) after 1 hour. A significant reversal was still observed after 24 hours in the 3 mg/kg (p=0.008) and 10 mg/kg (p=0.003) treated groups. For MK-801, the ANCOVA revealed no significant main effect of baseline (F1,27=0.03; p=0.86), a significant main effect of treatment (F3,27=9.60; p<0.001), a significant main effect of time (F1,28=31.14; p<0.001), and no significant treatment by time interaction (F3,28=0.90; p=0.452). Planned Comparisons revealed that MK-801 significantly reversed the CFA-induced hyperalgesia at 0.1 mg/kg (p=0.004) after 1 hour. A significant reversal was still observed after 24 hours in the 0.1 mg/kg (p<0.001) treated group.
Figure 22:
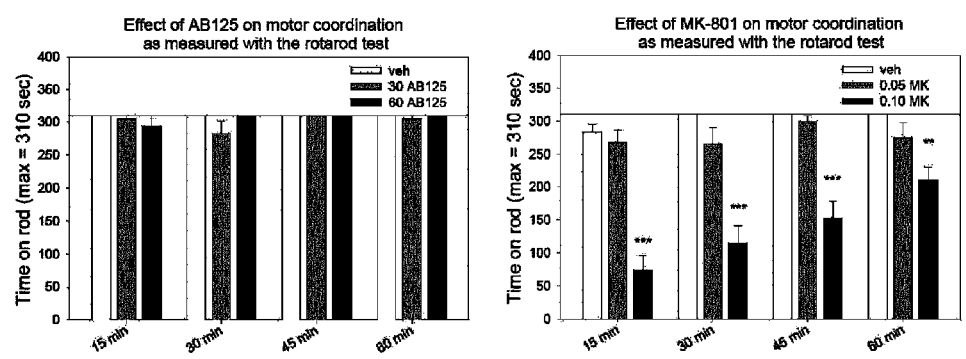
FIG. 22. Effect of AB125 and MK-801 on motor performance in the rotarod test. For AB125 (30 and 60 mg/kg shown), the two-way RM ANOVA showed no significant main effect of treatment (F2,48=1.18; p=0.333), no significant main effect of time (F3,48=0.84; p=4'79), and no significant treatment by time interaction (F6,48=1.26; p=0.293). For MK-801, the two-way ANOVA showed a significant main effect of treatment (F2,66=55.72; p<0.001), a significant main effect of time (F3,66=3.69; p=0.016), and a significant treatment by time interaction (F6,66=2.25; p=0.049). Planned Comparison revealed that 0.1 mg/kg MK-801 significantly decreased time on the rotarod at 15 min (p<0.001), 30 min (p<0.001), 45 min (p<0.001), and 60 min (p=0.006).
Figure 23:
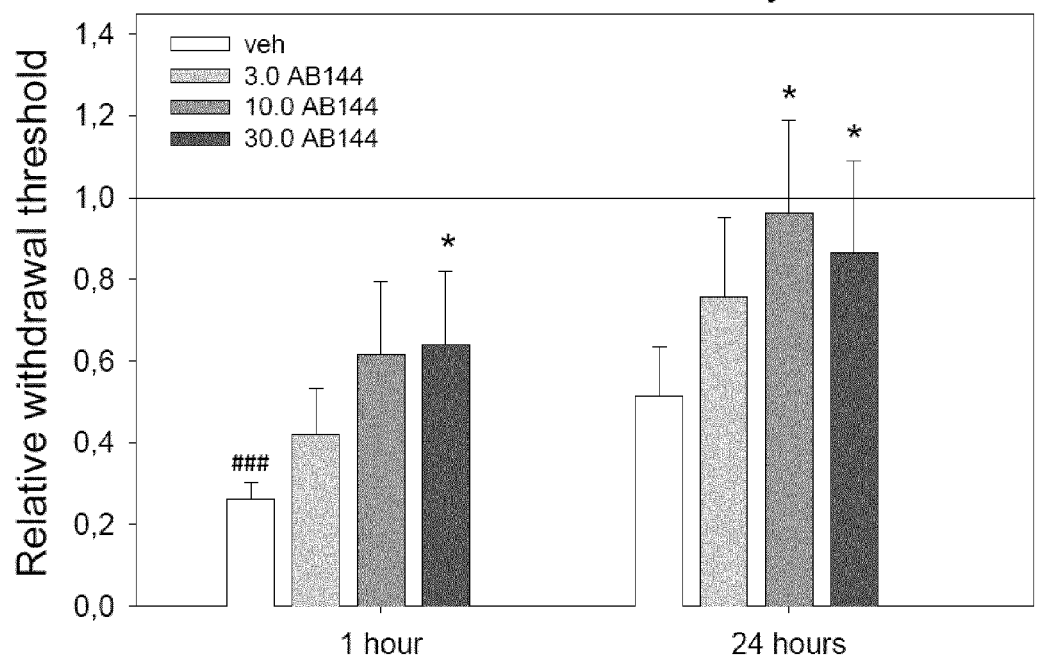
FIG. 23. Effect of AB144 in the complete Freund's adjuvant model of inflammatory pain. Animals were concurrently treated with intraplantar CFA and intraperitoneally AB144 (0, 3, 10, or 30 mg/kg), and mechanical hyperalgesia/allodynia was measured with the von Frey method 1 and 24 hours after. Data are expressed as mean±SEM, showing the paw withdrawal threshold relative to baseline values (i.e. <1.0 corresponds to hyperalgesia/allodynia). Saline-treated mice showed a marked response to CFA, with mechanical threshold reduced to 25% of baseline (###; p<0.001). This reduction was not observed 1 hour after AB144/CFA administration in mice treated with 30 mg/kg AB144, and at 24 hours after AB144/CFA administration in mice treated with 10 and 30 mg/kg AB144 (*: p<0.05).

When administered concurrently with CFA, both MK-801, AB125, and AB144 prevented the development of CFA-induced mechanical hyperalgesia 1 hour and 24 hours after treatment (FIGS. 17, 18, 23; Example 11). Moreover, AB125 was found to reverse CFA-induced hyperalgesia when administered 24 hours after CFA treatment, an effect lasting for at least 3 days (FIG. 19; Example 11). At the dose reducing the hyperalgesia, MK-801 induced cognitive deficits in the modified Y-maze and STFP tests as well as motor deficits in the rotarod test. Surprisingly, even high doses of AB125 were devoid of side-effects in these tests (FIG. 20-22; Example 11). The data show that dimeric PSD-95 inhibitors, without (AB125) and with (AB144) a CPP, are efficient in preventing and inhibiting the development of chronic inflammatory pain, while avoiding NMDA receptor antagonism-related side-effects on cognitive and motor function.

XI. Manufacture of a Pharmaceutical Composition Comprising a PSD-95 Inhibitor Formulations of a dimeric PSD-95 inhibitor or a CPP-containing dimeric PSD-95 inhibitor of the present invention into pharmaceutical compositions is well known in the art, and is further described in Gennaro (ed.), 2000, Remington: The Science and Practice of Pharmacy, 20th ed., Lippincott, Williams & Wilkins (2000); and Ansel et al., 1999, Pharmaceutical Dosage Forms and Drug Delivery Systems, 7th ed., Lippincott Williams & Wilkins Publishers.

Such a composition typically contains from about 0.1 to 90% by weight (such as about 1 to 20% or about 1 to 10%) of the PSD-95 inhibitor of the invention in a pharmaceutically accepted carrier.

Various liquid and powder formulations can be prepared by conventional methods for inhalation into the lungs of the mammal to be treated.

Compositions suitable for oral administration can be formulated by combining a dimeric PSD-95 inhibitor or a CPP-containing dimeric PSD-95 inhibitor of the invention with a suitable carrier as a tablet, pill, dragee, capsule, liquid, gel, syrup, slurry, suspension for oral ingestions by the subject to be treated. For solid oral/rectal formulations, suitable excipients include fillers such as sugars (e.g. lactose, sucrose, mannitol and sorbitol); cellulose preparations (e.g. maize starch, wheat starch, rice starch, potato starch, gelatin, gum tragacanth, methyl cellulose, hydroxypropylmethyl-cellulose, sodium carboxymethylcellulose, and/or polyvinylpyrrolidine; granulating agents; and binding agents. Optionally, disintegrating agents may be included, such as cross-linked polyvinylpyrrolidine, agar, or alginic acid or a salt of sodium alginate. The solid formulation may further include an enteric-coating.

For liquid oral formulations, suitable excipients or diluents include water, glycols, oils and alcohols.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water-soluble versions of the compounds can be administered by the drip method, whereby a pharmaceutical formulation containing the active agent (a CPP-containing dimeric PSD-95 inhibitor) and a physiologically acceptable excipient is infused. Physiologically acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the compound can be prepared and administered as a suspension in an aqueous base or a pharmaceutically acceptable oil base, such as an ester of a long chain fatty acid (e.g., ethyl oleate).

A dimeric PSD-95 inhibitor or a CPP-containing dimeric PSD-95 inhibitor of the invention may also be formulated as a long acting depot preparation. For example, the inhibitor may be formulated with suitable polymeric or hydrophobic materials (e.g. an emulsion of an acceptable oil) or ion exchange resin, or as a sparingly soluble derivative, such as a sparingly soluble salt.

Liposomes and emulsions may also be used to deliver the dimeric PSD-95 inhibitor or a CPP-containing dimeric PSD-95 inhibitor. Additionally, the inhibitor may be delivered via a sustained release system, such as semi-permeable matrices of solid polymers comprising the inhibitor.

The optimal percentage of the therapeutic agent in each pharmaceutical formulation varies according to the formulation itself and the therapeutic effect desired in the specific pathologies and correlated therapeutic regimens.

XII. Mode of Administration of a Pharmaceutical Composition Comprising a PSD-95 Inhibitor Conventional methods, known to those of ordinary skill in the art of medicine, can be used to administer compositions to the subject or patient, and may be supplied for use in the form of a kit. These include but are not limited to subcutaneous, intrapulmonary, transmucosal, intravenous, intraperitoneal, intrauterine, sublingual, intrathecal, or intramuscular routes, by using standard methods/means for delivery [including by injection, catheter, where the kit may include an injection devise, a devise for delivering an injectable depot, or a catheter]. In addition, the pharmaceutical formulations can be administered to the patient via injectable depot routes of administration such as by using 1-, 3-, or 6-month depot injectable or biodegradable materials and methods.

Regardless of the route of administration, a dimeric PSD-95 inhibitor or a CPP-containing dimeric PSD-95 inhibitor of the present invention is typically administered at a daily dosage of about 0.01 mg to about 120 mg/kg of body weight of the patient (e.g., 1 mg/kg to 20 mg/kg). The pharmaceutical formulation can be administered in multiple doses per day, if desired, to achieve the total desired daily dose.

Conventional methods, known to those of ordinary skill in the art of medicine, can be used to administer the pharmaceutical formulation(s) of the present invention to the patient. The pharmaceutical compositions of the present invention can be administered alone, or in combination with other therapeutic agents or interventions. Specifically, the compositions of the present invention may further comprise a plurality of agents of the present invention.

EXAMPLES

Example 1

Synthesis of Dimeric Inhibitors of PSD-95

Figure 16:
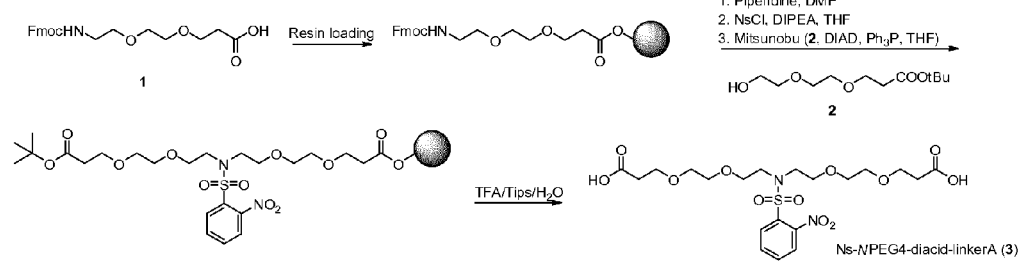
FIG. 16. Scheme 1. Synthesis of the NPEG-linker A-C in an N-protected (Ns) form (Ns-NPEG4-diacid-linkers), which is used in the dimerization process of making NPEG-based dimeric compounds. Ns-NPEG4-diacid-linkerA is used for AB141, AB144, AB147, AB144_D, AB144_E, AB143, AB145, and AB148. Ns-NPEG4-diacid-linkerB is used for AB144_B. Ns-NPEG4-diacid-linkerC is used for AB144_C.
Figure 16:
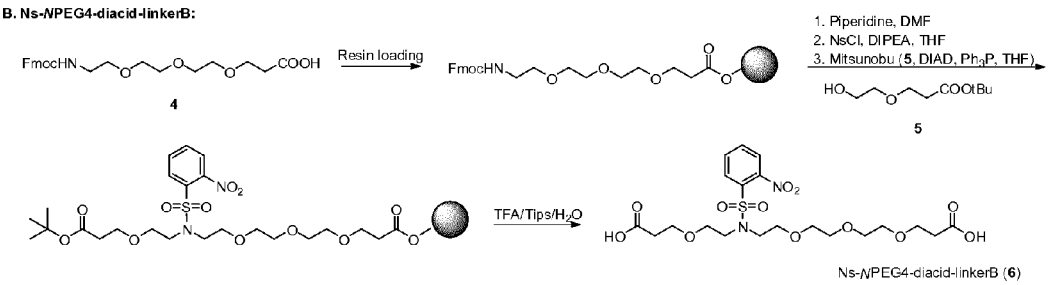
Figure 16:
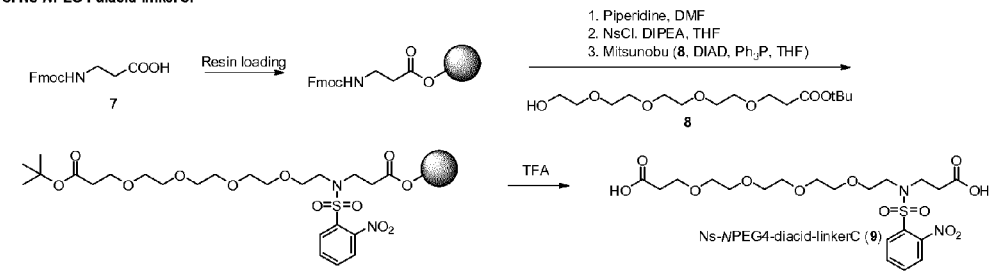

1.1 Synthesis of the Ns-NPEG4-diacid-linkerA-C (Scheme 1—FIG. 16)

For the synthesis of Ns-NPEG4-diacid-linkerA (3; Scheme 1) 2-chlorotrityl chloride resin (3 mmol, 1.90 g) was washed and swelled (20 min) in DMF. Fmoc-NH-PEG$_2$-CH$_2$CH$_2$COOH (1, Scheme 1; Biomatrik Inc., Jiaxing, China) was loaded onto the resin by adding 1 (2 mmol, 800 mg) in DMF (8 mL) to the drained resin followed by DIPEA (10 mmol, 1.75 mL). After shaking for 60 min, methanol (1 mL, 25 mmol) was added, and shaking was continued for another 5 min. The loaded resin was drained and washed thoroughly with DMF (10-15 flow washes, each of 10 mL), and the Fmoc group was de-protected with 20% piperidine in DMF for 5 min and 15 min with a DMF wash in between, followed by a DMF and THF wash. The resin was swelled in DIPEA (12 mmol, 2.1 mL) and THF (8 mL) for 15 min, and ortho-nitrobenzenesulfonyl chloride (NsCl, 8 mmol, 1.78 g) in DCM (5 mL) was added slowly while gently stirring the resin. After 4 hours, the resin was drained and washed consecutively with THF, MeOH, DCM, and THF. The resin-attached free amino group was alkylated with the alcohol HO-PEG$_2$-CH$_2$CH$_2$COOtBu (2, Scheme 1; Biomatrik Inc., Jiaxing, China) starting by evacuating the reaction vessel and adding a nitrogen balloon. The resin (1 eq., 2 mmol) was treated with triphenylphosphine (PPh$_3$, 10 mmol, 2625 mg) in THF (5 mL) and 2 (10 mmol, 2.34 g) in THF (5 mL). Diisopropyl azodicarboxylate (DIAD) (10 mmol, 2.02 g, 1.97 mL) was added dropwise, and the balloon was removed before shaking for 1 hour. The resin was thoroughly washed with THF and DCM, dried in vacuo and treated with TFA/triisopropylsilane/H$_2$O (90/5/5, 20 mL) for 2.5 hours. The TFA-mixture was collected and the resin was washed with TFA and DCM before the combined TFA/DCM fractions were evaporated and co-evaporated with ether (2×30 mL). The resulting material was dissolved in water/MeCN (75/25, 100 mL) and lyophilized to get Ns-NPEG4-diacid-linkerA (3, Scheme 1) as an orange oil, which was used directly in the synthesis of dimeric NPEG4 ligands. Yield: 80%. m/z (ESI) 540.1 (22%), 523.1 (M$^+$+H, 100), 505.1 (11), 433.0 (7.3), 365.2 (7.4).

The procedure used for the synthesis of Ns-NPEG4-diacid-linkerA was also used to synthesize Ns-NPEG4-diacid-linkerB and Ns-NPEG4-diacid-linkerC (6 and 9, respectively; Scheme 1). For making Ns-NPEG4-diacid-linkerB (6), building blocks Fmoc-NH-PEG$_3$-CH$_2$CH$_2$COOH (4; Biomatrik Inc., Jiaxing, China) and HO-PEG$_1$-CH$_2$CH$_2$COOtBu (5; Biomatrik Inc., Jiaxing, China) were used (Scheme 1). Yield: 54%. m/z (ESI) 596.2 (22%), 523.2 (M$^+$+H, 100), 505.1 (15), 433.1 (8).

For making Ns-NPEG4-diacid-linkerC (9), building blocks Fmoc-beta-alanine (7; Sigma-Aldrich, St. Louis, Mo.) and HO-PEG$_4$-CH$_2$CH$_2$COOtBu (8; IRIS Biotech, Marktredwitz, Germany) were used (Scheme 1). Yield: 45%. m/z (ESI) 596.2 (51%), 523.1 (M$^+$+H, 100), 506.1 (14), 433.1 (55).

1.2 Synthesis of Peptide Moieties of Dimeric Inhibitors of PSD-95

Peptides (e.g. IETDV (SEQ ID NO: 18) or IETAV (SEQ ID NO: 16)) were synthesized by Fmoc-based solid phase peptide chemistry using preloaded Fmoc-Val-Wang-resin (0.6-0-7 mmol/g, 100-200 mesh), HBTU/DIPEA for couplings, and dry DMF as solvent. Each coupling was carried out for 40 min with a 1/4/3.9/8 stoichiometry of resin/Fmoc-amino acid/HBTU/DIPEA, and was qualitatively evaluated by the ninhydrin test. Fmoc-deprotection was carried out in 20% piperidine in DMF for 5 min, followed by DMF wash and a second piperidine/DMF treatment for 15 min.

1.3 Synthesis of NPEG4-based Dimeric Ligands AB141, AB144 and AB147 (FIGS. 2 and 3)

Ns-NPEG4-diacid-linkerA (3, Scheme 1; 0.1 eq., 0.025 mmol) was pre-activated with HBTU (0.2 eq, 0.05 mmol) and DIPEA (0.4 eq, 0.1 mmol) and added to Fmoc-deprotected Wang-resin-bound IETDV (SEQ ID NO: 18) (1 eq, 0.25 mmol) in a total volume of 4 mL DMF. The reaction was shaken for 45 min and repeated 5 times. The Ns group was removed by adding DBU (0.5 mmol) in DMF (2 mL) followed by mercaptoethanol (0.5 mmol) in DMF (2 mL). The reaction was shaken for 30 min and washed in DMF. Treatment with mercaptoethanol/DBU was repeated once, and the resin washed consecutively with DMF, DCM, MeOH and DCM to provide resin-bound AB141. For AB144 and AB147 the first amino acid of the CPP (L- or D-Arg, respectively) was coupled to the nitrogen by six consecutive couplings of Fmoc-Arg(Pbf)-OH. For each coupling, Fmoc-Arg(Pbf)-OH (0.5 mmol) was activated by HATU in DMF (2 mL, 0.244 M) and collidine (132 µL), before adding it to the drained resin. After 40 minutes of shaking and a DMF wash, the coupling and DMF wash was repeated 5 times followed by a thorough DMF wash. Fmoc was removed with 20% piperidine in DMF, the remaining Tat- or Retroinverso-D-Tat sequence synthesized as described for peptide synthesis, and the final Fmoc group removed.

1.4 Synthesis of NPEG4-based Dimeric Ligands AB144-B and AB144-C (FIG. 15)

AB144_B and AB144_C were synthesized as described for AB144, except that Ns-NPEG4-diacid-linkerB and Ns-NPEG4-diacid-linkerC were used, respectively, instead of Ns-NPEG4-diacid-linkerA.

1.5 Synthesis of NPEG4-based Dimeric Ligands AB144-D and AB144-E (FIG. 15)

The synthesis of AB144_D and AB144_E was as described for AB144 up to the point where resin-bound AB141 is provided. Fmoc-Gly-OH was coupled to the nitrogen atom on the NPEG4-linker by six consecutive couplings with HBTU/DIPEA as described above in the peptide synthesis section, 1.2. After Fmoc removal with piperidin/DMF, N-Maleoyl-β-alanine (Sigma-Aldrich, St. Louis, Mo.) was coupled (HBTU/DIPEA) to half the resin, which was subsequently dried in vacuo and treated with cleaving-mix TFA/thioanisole/$H_2O$/anisole 90/5/3/2 (v/v/v/v) to provide crude maleimide-dimer intermediate. In parallel, the 12-mer peptide Tat-Cys (Sequence: YGRKKRRQRRRC (SEQ ID NO: 13)) was prepared by standard Fmoc-based peptide synthesis starting from a 2-chlorotrityl chloride resin loaded with Fmoc-Cys (Trt)-OH followed by cleavage from the resin. AB144_D was next synthesized by mixing 0.05 mmol crude maleimide-dimer intermediate with 0.06 mmol crude Tat-Cys in 10 mL acetonitrile and 50 mL TBS buffer (50 mM Tris-HCl, 150 mM NaCl, pH 7.4, degassed) at room temperature, the pH was adjusted to 7 with NaOH (0.2 M), and the reaction mixture was incubated for 90 minutes. The mixture was then freeze-dried and pure AB144_D was provided by HPLC purification.

1.6 Synthesis of PEG4-based Dimeric Ligands AB144-H and AB144-I

Compounds AB144_H and AB144_I were synthesized from a preloaded Val-wang-resin starting by making the resin-bound peptide sequences, K(Dde)ETDV (SEQ ID NO: 19) and K(Dde)IETDV (SEQ ID NO: 20), respectively [Sidechains of E, T, D are protected with tert-butyl groups while compound is resin-bound; K is protected with Dde: 1-(4,4-dimethyl-2,6-dioxocyclohex-1-ylidene)ethyl], as described in the 'Peptide synthesis (General)' section. The on-resin dimerization process was carried out with the PEG4-diacid linker (IRIS Biotech, Marktredwitz, Germany) as described previously (WO2010/004003). Next, Dde was removed by treating the resin with freshly prepared hydrazine monohydrate (2% in DMF) for 5 minutes, followed by a DMF wash and another hydrazine treatment for 10 minutes. The resin was thoroughly washed with DMF, 10% DIPEA in DMF (5×2 minutes), DCM, and DMF consecutively. The Tat sequence was synthesized from the liberated amino group at the lysine side-chain using HATU/Collidine and standard removal of Fmoc with piperidine/DMF.

Example 2

Synthesis of Labeled Analogues of Dimeric Inhibitors of PSD-95

2.1 Synthesis of Fluorophore-labeled Analogues (AB143, AB145, AB148, MS23)

Fluorescent ligands were prepared by coupling 5-FAM (5-carboxyfluorescein; Anaspec, San Jose, Calif., USA) to the N-terminal amino group of the final and Fmoc-deprotected AB144, AB147, or Tat-NR2B9c, while bound to the resin, to produce AB145, AB148, and MS23, respectively. Likewise, 5-FAM was coupled to Ns-deprotected, resin-bound AB141 to produce AB143. 5-FAM was coupled in a 1/2/2/3 ratio of N-sites-resin/5-FAM/HATU/collidine in a total of 2 mL DMF at a 0.07 mmol scale (molar of NPEG-linker). For AB145, AB148, or MS23, coupling time was 6 hours. For AB143, 5-FAM was coupled by two consecutive couplings of 6 and 16 hours, respectively.

2.2 Synthesis of $^{15}N$, $^{13}C$-labeled Dimeric Ligand of PSD-95

[$^{15}N$, $^{13}C$]-PEG4(IETAV)$_2$ (SEQ ID NO: 16) (AB140) was synthesized using Fmoc-protected amino acids containing fully $^{15}N$, $^{13}C$-labeled amino acid atoms (Cambridge Isotope Laboratories, Inc., Andover, Mass., USA). Amino acid building blocks for Thr and Glu were side chain protected with tert-butyl groups. Labeled Fmoc-Val-OH (0.125 mmol, 43 mg) was dissolved in DMF (1.5 mL) and loaded to the 2-chlorotrityl chloride resin (0.1875 mmol, 119 mg) that had been swelled in DMF (2 mL) for 20 min and drained. DIPEA (0.625 mmol, 109 µL) was added and shaking was continued for 60 min. MeOH (100 µL) was added, and shaking was continued for 15 min, and the resin washed with DMF. Fmoc was removed with piperidein/DMF and labeled IETAV (SEQ ID NO: 16 ) was further synthesized using coupling conditions and stoichiometries of 1/2/2/3 of resin/Fmoc-amino acid/HATU/collidine in DMF (1 mL) for 40 min. After the final Fmoc-removal, the resin was washed with DMF and DCM, dried in vacuo and used further to prepare AB140 by the on-resin dimerization process with the (unlabeled) PEG4-diacid linker (IRIS Biotech, Marktredwitz, Germany) described previously (WO2010/004003).

Example 3

Purification and Characterization of Dimeric PSD-95 Inhibitors of PSD-95 and Labeled Derivatives Thereof Synthesized compounds, including dimeric PSD-95 inhibitors and derivatives thereof, were obtained as TFA salts by treating the resin-bound products with trifluoroacetic acid (TFA)/triisopropylsilane/$H_2O$ (90/5/5) for 2 hours (unless other specification is stated), evaporation in vacuo, precipitation with cold ether, lyophilization, and purification with preparative reverse phase high-performance liquid chromatography (RP-HPLC). Compounds were characterized by analytical HPLC and mass spectrometry (Table 1).

TABLE 1

Characterization of compounds.

| Compounds | Formula | $M_w$ | m/z[1] | Purity[2] |
|---|---|---|---|---|
| IETDV (SEQ ID NO: 18) | $C_{24}H_{41}N_5O_{11}$ | 575.6 | 576.4 [M + H]$^+$ | >98% |
| AB141 | $C_{60}H_{105}N_{11}O_{24}$ | 1364.5 | 1364.7 [M + H]$^+$ | >98% |
| AB144 | $C_{126}H_{221}N_{43}O_{41}$ | 2994.4 | 599.8 [M + 5H]$^+$ | >98% |

TABLE 1-continued

Characterization of compounds.

| Compounds | Formula | $M_w$ | m/z[1] | Purity[2] |
|---|---|---|---|---|
| AB147 | $C_{115}H_{209}N_{41}O_{38}$ | 2774.1 | 555.9 [M + 5H]$^+$ | >98% |
| Tat-NR2B9c | $C_{105}H_{188}N_{42}O_{30}$ | 2518.9 | 504.7 [M + 5H]$^+$ | >98% |
| AB143 | $C_{81}H_{115}N_{11}O_{30}$ | 1722.8 | 862.1 [M + 2H]$^+$ | >98% |
| AB145 | $C_{147}H_{231}N_{43}O_{47}$ | 3352.7 | 671.5 [M + 5H]$^+$ | >98% |
| AB148 | $C_{136}H_{219}N_{41}O_{44}$ | 3132.4 | 627.5 [M + 5H]$^+$ | >98% |
| MS23 | $C_{126}H_{198}N_{42}O_{36}$ | 2877.2 | 576.4 [M + 5H]$^+$ | >98% |
| AB140[3] | $C_{60}H_{104}N_{10}O_{25}$ | 1421.1 | 711.2 [M + 2H]$^+$ | >98% |
| AB144_B | $C_{126}H_{221}N_{43}O_{41}$ | 2994.4 | 599.8 [M + 5H]$^+$ | 95% |
| AB144_C | $C_{126}H_{221}N_{43}O_{41}$ | 2994.4 | 599.8 [M + 5H]$^+$ | 95% |
| AB144_D | $C_{138}H_{236}N_{46}O_{47}S$ | 3323.7 | 665.7 [M + 5H]$^+$ | >98% |
| AB144_E | $C_{134}H_{234}N_{46}O_{45}S_2$ | 3273.7 | 655.8 [M + 5H]$^+$ | 96% |
| AB144_H | $C_{190}H_{338}N_{76}O_{55}$ | 4567.2 | 508.4 [M + 9H]$^+$ | 96% |
| AB144_I | $C_{202}H_{360}N_{78}O_{57}$ | 4793.5 | 533.5 [M + 9H]$^+$ | 95% |

[1]Most abundant ion is listed (ESI-LC/MS).
[2]Analytical HPLC (UV$_{218}$) and ESI-LC/MS (ELSD) were conducted for all compounds to determine purity.
[3]Peptide part, IETAV (SEQ ID NO: 16), is [$^{15}$N, $^{13}$C]-labeled.

For in vivo experiments, compounds were prepared as HCl salts by incubating the TFA salts of the compounds with ice cold aq. HCl (50 mM; 3-fold molar excess of HCl relative to TFA) for 20 min followed by lyophilization.

3.1 Preparative RP-HPLC:
Compounds were purified on a Agilent 1200 system with a C18 reverse phase column (Zorbax 300 SB-C18, 21.2×250 mm) using a linear gradient of H$_2$O/MeCN/TFA (A: 95/5/0.1 and B: 5/95/0.1) and a flow rate of 20 mL/min.

3.2 ESI-LC/MS:
Mass spectra were obtained with an Agilent 6410 Triple Quadrupole Mass Spectrometer instrument using electron spray ionization (ESI), coupled to an Agilent 1200 HPLC system (ESI-HPLC-MS) with a C18 reverse phase column (Zorbax Eclipse XBD-C18, 4.6×50 mm), evaporative light scattering detector (ELSD, Sedere Sedex 85) and a diode-array detector (UV) using a linear gradient of H$_2$O/MeCN/Formic Acid (A: 95/5/0.1 and B: 5/95/0.086) with a flow rate of 1 mL/min.

3.3 Analytical RP-HPLC: Compound purities were determined by an Agilent 1100 system with a C18 reverse phase column (Zorbax 300 SB-C18 column, 4.6×150 mm) using a linear gradient of H$_2$O/MeCN/TFA (A: 95/5/0.1 and B: 5/95/0.1) and a flow rate of 1 mL/min.

3.4 High Resolution Mass Spectra (HRMS): HRMS were obtained for AB144 and AB147 using electron spray ionization (ESI) and a Micromass Q-T of 2 instrument.

Example 4

Expression and Purification of PDZ1-2 of PSD-95

The cDNA coding for PSD-95 PDZ1-2 tandem (corresponding to residues 61-249 in the human full-length PSD95α without exon 4b) were amplified by inverted PCR and cloned in a modified His-tagged pRSET vector (Invitrogen, Carlsbad, Calif., USA). The encoded PDZ1-2 peptide further comprised the sequence, MHHHHHPRGS (SEQ ID NO: 14), which was used as a tag for purification (His-tag), and the DNA coding sequences and encoded proteins are designated as follows: HIS-PDZ1-2 DNA [SEQ ID NO: 1] encoding HIS-PDZ1-2 protein [SEQ ID NO: 2]. Competent E. coli bacteria (BL21-DE3, pLysS) were transformed with PDZ1-2 expressing construct and grown overnight on agar plates containing ampicillin (100 µg/mL) and chloramphenicol (35 µg/mL) at 37° C. Colonies were picked and used to inoculate bacterial cultures (LB medium with 50 µg/mL ampicillin). These were shaken while being incubated at 37° C. until A$_{600}$ of the culture reached 0.45, at which point 1 mM isopropyl β-D-1-thiogalactopyranoside was added. Induced cultures were incubated over night at 30° C. (PDZ1-2). Cells were harvested by spinning at 10,000 g for 10 min at 4° C. and re-suspended in lysis buffer (50 mM Tris/HCL pH 7.5, 1 mM PMSF, 25 µg/ml DNAse, 40 mM Mg$_2$SO$_4$). The cells were destroyed using a cell disruptor apparatus at 26 KPsi. The cell lysate was spun down at 35,000 g for 1 hour and the supernatant filtered with a 0.45 µm and a 0.22 µm filter. Purification of expressed PDZ1-2 peptide was performed with first a nickel (II)-charged column (HisTrap™ HP, GE Healthcare, UK) equilibrated with Tris-buffer (Tris/HCl buffer 50 mM, pH 7.5) followed by gel-filtration. For gel-filtration the PDZ1-2 sample was loaded on a Superdex™ 75 HR 10/30 column (GE Healthcare, UK) equilibrated with Tris buffer (20 mM Tris/HCL, pH 7.5) with a constant flow rate at 0.5 mL/min. The relevant fractions were analyzed on a SDS-PAGE gel stained by a standard silver staining protocol. The final purification was analyzed by electrospray ionization liquid chromatography-mass spectrometry (ESI-LC/MS) to get the exact molecular weight and thereby verify the identity of the PDZ1-2 domain. Molar extinction coefficients were found by amino acids analysis (Alphalyse, Odense, Denmark) and thereafter used for measuring protein concentrations. For NMR studies, uniformly labeled [$^{15}$N] PDZ1-2 was expressed by growing the bacterial culture in M-9 media followed by purification as described above.

Example 5

Enhanced Affinity Dimeric PSD-95 Inhibitors for the PDZ Domain of PSD-95

5.1 Fluorescence Polarization (FP) Assay for Determining the Affinity of Ligands (Dimeric PSD-95 Inhibitors) for the PDZ Domain of PSD-95

An in vitro affinity measurement assay was developed based on the fluorescence polarization principle in order to provide affinity constants ($K_i$ values) between synthesized ligands (e.g. dimeric inhibitors) and PDZ1-2 of PSD-95. First, affinity between the 5-FAM-labeled NPEG4(IETAV)$_2$ (SEQ ID NO: 16) probe, designated AB143 (FIG. 4), and PDZ1-2 was established by a saturation binding experiment, where increasing concentrations of PDZ 1-2 was added to a fixed concentration (0.5 nM) of the probe. The assay was performed in TBS buffer (150 mM NaCl, 10 mM Tris, pH 7.4) in black, flat bottom 384-well plates (Corning Life Sciences, NY, USA). After incubation for 10 min at room temperature, fluorescence polarization of the samples was measured on a Safire2 plate-reader (Tecan, Männedorf, Switzerland) at excitation/emission values of 470/525 nm. The fluorescence polarization values were fitted to the equation $Y = B_{max} \times X / (K_d + X)$, with $B_{max}$ being the maximal fluorescence polarization value, X is the PDZ1-2 concentration, and Y is the fluorescence polarization value. $K_d$ was directly derived from the saturation curve as being equal to the PDZ1-2 concentration at half-saturation, and found to be 7.8±0.11 nM, which is in good agreement with the $K_i$ value found for its corresponding non-fluorescent ('cold') ligand, AB141 ($K_i$=9.3±1 nM). The affinities between non-fluorescent compounds and PDZ1-2 were determined by heterologous competition, where increasing concentrations of compound were added to a fixed concentration of probe (0.5 nM) and PDZ1-2 (7.8 nM) in the same TBS buffer and conditions as described above. FP values were fitted to the general equation: $Y = Bottom + (Top - Bottom)/[1+(10^{(X-Log\,IC_{50}*HillSlope)})]$, where X is the logarithmic value of peptide concentration, and the resulting IC$_{50}$ values were converted to competitive inhibition constants, $K_i$ values. All values reported are the average of at least three individual experiments. Ligand stocks were prepared in water and concentrations were verified by amino acid analysis.

5.2 Dimeric PSD-95 Inhibitors of the Invention have Enhanced Affinity for the PDZ1-2 Domain The FP assay (see 5.1) was employed to determine the affinity of various dimeric PSD-95 inhibitors for the PDZ1-2 domain of PSD-95. The dimeric inhibitor AB141 differs from AB125 in that the PEG4 linker is substituted by an NPEG4 linker. This difference has no significant effect on the affinity of the dimeric inhibitor for PDZ 1-2, since both displayed $K_i$ values around 9.5 nM (FIG. 5). The addition of a CPP to the dimeric inhibitor AB141, where the CPP is attached to the NPEG4 linker, results in a surprising increase in affinity for PDZ1-2. AB144 (CPP is Tat) and AB147 (CPP is Retroinverso-D-Tat) showed a 2-fold increase over AB141 in $K_i$ value=4.6±0.3 and 5.1±0.4 nM, respectively (FIG. 5), and a 1000-fold increased affinity relative to the monomeric Tat-NR2B9c peptide ($K_i$=4600±300 nM against PDZ1-2 of PSD-95; FIG. 5).

5.3 CPP-containing Dimeric PSD-95 Inhibitors have Enhanced Affinity for the PDZ1-2 Domain The AB144 analogues (see Example 1 and FIG. 15) AB144_B and AB144_C, in which the point of Tat-attachment to the NPEG linker nitrogen atom is asymmetric (either one or two 'ethylene glycol moieties' away from the center of the linker), showed affinities towards PDZ1-2 of PSD-95 in the same range as AB144, i.e. in the low nanomolar range (Table 2). Although AB144_C demonstrates a 2-fold greater affinity compared to AB144 both compounds are highly potent ligands for the PDZ1-2 domain.

The AB144 analogues (see Example 1 and FIG. 15) AB144_D and AB144_E, Tat is attached symmetrically to the NPEG linker, but in AB144_D, Tat is attached by a maleimide coupling, while in AB144_E, Tat is attached via an disulfide (S—S) bond. Although AB144_D and AB144_E displayed ~2-3 fold lower affinity than AB144 (Table 2), their $K_i$ values were still in the lower nanomolar range, and hence compounds are still very strong binders to PDZ1-2 of PSD-95.

In compound AB144_H and AB144_I (see Example 1 and FIG. 15), the Tat-sequence is attached to an amino acid side chain of one of the PEG-linked dimeric peptides, instead of using an NPEG linker. In AB144_H, the Tat extends from the $P^{-4}$ amino acid, which in this case is a lysine. Normally isoleucine (I) is found in this position (AB144), but here lysine is used, as it provides a functional group (amino group) from where the Tat can be synthesized, and still functions as a structural analogue for isoleucine (alkane based, non-charged after amide bond formation to the first Tat amino acid, similar in size). AB144_H retains a nanomolar affinity to PDZ1-2, although slightly less optimal being ~5-fold lower than that of AB144 (Table 2). In AB144_I the Tat is attached to the side chain of the $P^{-5}$ amino acid in a hexapeptide, and shows greater affinity for the PDZ1-2 domain than AB144_H, although ca 2-fold weaker than AB144 (Table 2).

TABLE 2

$K_i$ affinity constants of AB144 analogues towards PDZ1-2 of PSD-95 as measured by fluorescence polarization. Data represents ≥4 individual measurements.

| Compound | $K_i$ ± SEM (nM) |
| --- | --- |
| AB144_B | 5.2 ± 0.3 |
| AB144_C | 2.3 ± 0.2 |
| AB144_D | 9.9 ± 0.5 |
| AB144_E | 16 ± 0.6 |
| AB144_H | 24 ± 2 |
| AB144_I | 12 ± 1 |

Example 6

Modified Dimeric PSD-95 Inhibitors have Enhanced Stability in Human Blood Plasma 6.1 Human Blood Plasma Stability Assay Ligands (dimeric PSD-95 inhibitors) for the PDZ domain of PSD-95 were dissolved in human blood plasma (270 µL; 3H Biomedical, Sweden, cat no 1300-1-P50) to a concentration of 0.25 mM (30 µL, of 2.5 mM) and incubated at 37° C. Aliquots (30 µL) were removed at various time intervals (e.g. 0, 5, 10, 20, 40, 80, 160, 320, 960, 1280, 2550, 4560 and 7240 min) and quenched with 60 µL, trichloroacetic acid (aq., 5%). The aliquots were vortexed, and incubated 15 min, at 4° C. prior to centrifugation at 18,000 g for 2 min. The supernatants were analyzed by analytical RP-HPLC ($UV_{218}$) to quantify compound relative to time zero, and also evaluated qualitatively by ESI-LC/MS in order to identify the compound (m/z) in the sample. Procaine (positive control) and procainamide (negative control) were investigated at 50 µM to validate the procedure. Ligand recoveries following the precipitation procedure were between 85-95%.

6.2 Enhanced Blood Plasma Stability of Dimeric Inhibitors Having a Tat Peptide

The dimeric inhibitors AB144 (CPP is Tat) and AB147 (CPP is Retroinverso-D-Tat) were incubated in human blood plasma and their degradation in vitro was monitored. When compared with susceptibility to degradation of the monomeric pentapeptide IETDV (SEQ ID NO: 18) and Tat-NR2B9c, which showed half-lives ($T_{1/2}$) of 37±6 and 1100±300 minutes, respectively, AB144 displayed a $T_{1/2}$=4900±100, which corresponds to a more than 100-fold improvement in stability compared to the monomeric pentapeptide IETDV (SEQ ID NO: 18) (FIG. 5). No detectable degradation of AB147 was observed within the period of measurements (130 hours) (FIG. 5), illustrating the effect of introducing a protease-stable CPP into the dimeric inhibitor.

Example 7

Dimeric PSD-95 Inhibitors Bind to Both PDZ1 and PDZ2 Domains of PSD-95

7.1 NMR Analysis of Ligand Binding to Both PDZ1 and PDZ2 Domains of PSD-95

An NMR sample comprising 3.5 mM free [$^{15}$N, $^{13}$C]-PEG4(IETAV)$_2$ (SEQ ID NO: 16) (AB140) and 2.2 mM of the same compound saturated with unlabeled PDZ1-2 in 50 mM KPi, pH 7.5 in 90% $H_2O$/10% $D_2O$ was prepared for binding studies. All experiments were recorded at 25° C. at a static magnetic field corresponding to a proton Larmor frequency of 600 MHz. HNCA, HN(CA)CO and HSQC experiments were recorded to assign the backbone of the peptide moieties of the free compound. For the bound compound HNCACB, HN(CA)CO and HSQC experiments were recorded for assignment purposes.

$^{15}$N $R_1$ and $R_{1\rho}$ relaxation rates as well as the $^{15}$N-[$^1$H] NOE were measured for 2.83 mM [$^{15}$N]-PDZ1-2 saturated with unlabeled AB125 using previously described pulse sequences. Sample conditions were as above. For the $R_1$ experiment the following relaxation delays were used: 0.01, 0.05, 0.1, 0.2, 0.3, 0.4, 0.5, 0.6, 0.7, 0.8, 0.9, 1.0 sec. Uncertainties in peak intensities were estimated from five duplicate data points. The $R1_\rho$ experiment was recorded with a spinlock field of 1661 Hz and the radiofrequency carrier positioned at 119 ppm and relaxation delays of 0.004, 0.008, 0.012, 0.016, 0.0,02, 0.024, 0.03, 0.036, 0.04, 0.05, 0.055, 0.06 sec. Five duplicate data points were recorded for estimation of uncertainties in peak volumes. $^{15}$N-[$^1$H] NOE was recorded by taking the ratio of experiments recorded with and without saturating the protons. The total recycle delay for both experiments was 12 sec and the experiment without the saturation pulses was duplicated for estimation of uncertainties.

All NMR data were processed with NMRpipe and visualized using Sparky (Goddard and Kneller, University of California at San Francisco). Assignments for the bound form of PDZ1-2 were obtained by transferring the assignments from PDZ1-2/cypin (Wang et al., J. Am. Chem. Soc. 131, 787, 2009). Since a different compound was used in this study and since sample conditions were different, only slightly more than half of the assignments could be transferred with confidence. The remaining peaks in the spectra were not analyzed. Peaks were integrated and volumes converted into relaxation rates using the in house program PINT. The same program was used to convert $R_{1\rho}$ relaxation rates into $R_2$ relaxation rates.

7.2 Dimeric PSD-95 Inhibitors Bind to Both PDZ1 and PDZ2

Figure 6:
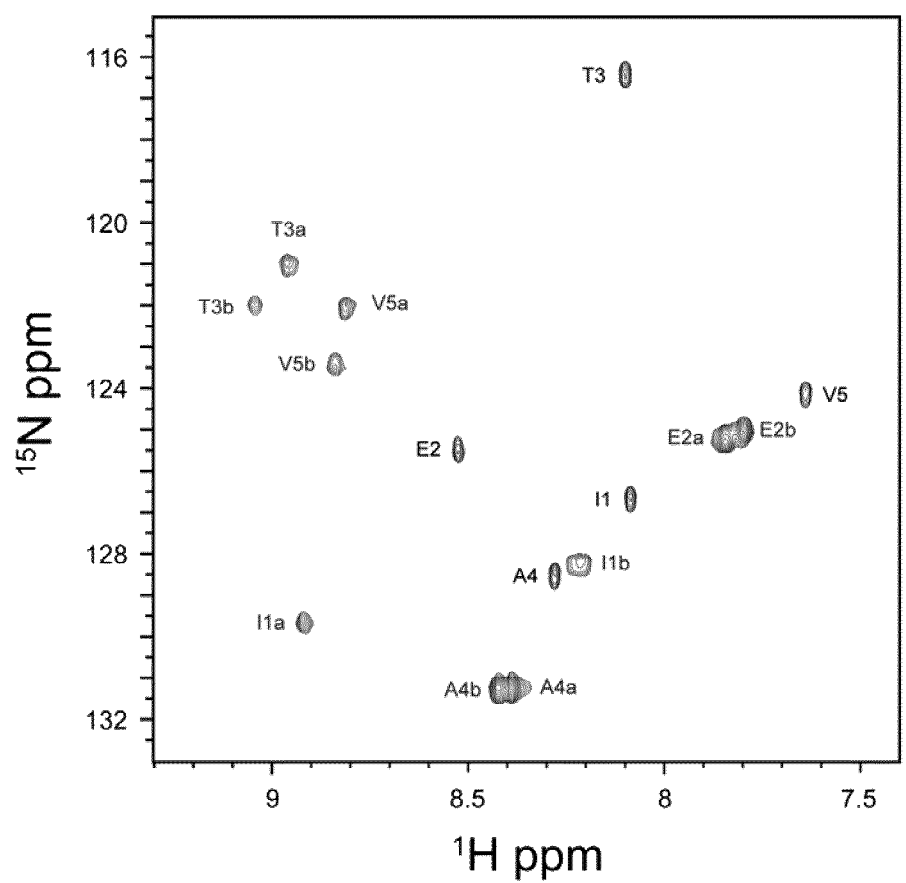
Figure 7:
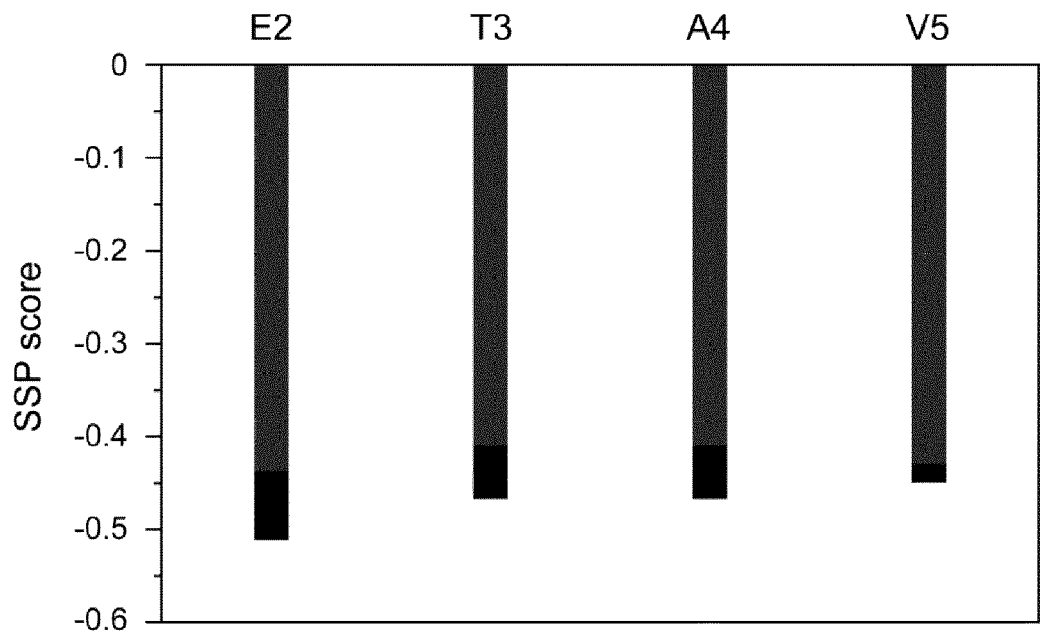
FIG. 7. Secondary structure propensities of the bound form of AB140 as calculated using the program SSP. A value of one indicates a fully formed α-helix and a value of minus one indicates a fully extended structure whereas a value close to zero is indicative of a random coil. Black bars correspond to residues labeled 'a' and grey bars to residues labeled 'b' in FIG. 6.

Binding of the $^{15}$N, $^{13}$C-labeled dimeric ligand (AB140) to PDZ1 and PDZ2 was analysed by determining its NMR structure in the presence/absence of unlabeled PDZ1-2, as described in 7.1. Five peaks were detected in an HSQC spectrum for the symmetrical ligand [$^{15}$N, $^{13}$C]-PEG4(IETAV)$_2$ (SEQ ID NO: 16) (AB140). However, when the ligand was combined with PDZ1-2, ten different peaks corresponding to each of the ten amino acids were observed (FIG. 6). This clearly demonstrates that both ligand moieties interact with PDZ1-2 and that they face different protein environments, namely PDZ1 and PDZ2, respectively. From secondary structural calculations based on the chemical shifts for the bound and unbound dimeric ligand it can be deduced that the unbound ligand exhibits random coil character, while the bound ligand adopts a β-stranded structure (FIG. 7). Finally, $R_1$ and $R_2$ relaxation rate measurements confirmed that PDZ 1-2 in complex with dimeric ligand tumbles as one unit, and thus ruling out other potential models such as a 2:2 binding stoichiometry (Table 3). Accordingly, the NMR studies confirm a 1:1 binding stoichiometry and unambiguously demonstrate that each ligand moiety of the dimeric ligand either bind PDZ1 or PDZ2 in PDZ1-2 in a truly bivalent binding mode.

TABLE 3

$^{15}$N $R_1$ and $R_2$ relaxation rates and $^1$H-$^{15}$N NOE measured for [$^{15}$N]-PSD95 PDZ1-2 in complex with AB125. Only results for residues where the assignments could be transferred with confidence from Wang et al., J. Am. Chem. Soc. 131, 787, 2009 are shown.

| Residue | $R_1$ (s$^{-1}$) | $R_2$ (s$^{-1}$) | NOE |
|---|---|---|---|
| I6 | 1.10 ± 0.02 | 15.0 ± 0.4 | 0.56 ± 0.02 |
| T7 | 0.95 ± 0.03 | 15.2 ± 0.6 | 0.70 ± 0.08 |
| G11 | 1.60 ± 0.49 | 15.4 ± 0.6 | 0.50 ± 0.01 |
| G14 | 0.98 ± 0.05 | 13.3 ± 0.8 | 0.45 ± 0.01 |
| G16 | 1.01 ± 0.03 | 16.8 ± 0.8 | 0.83 ± 0.02 |
| F17 | 1.03 ± 0.02 | 19.7 ± 0.6 | 0.66 ± 0.06 |
| T23 | 0.98 ± 0.02 | 18.7 ± 0.7 | 0.80 ± 0.00 |
| D24 | 1.08 ± 0.04 | 18.7 ± 0.7 | 0.83 ± 0.01 |
| N25 | 1.06 ± 0.03 | 17.0 ± 0.7 | 0.65 ± 0.01 |
| H27 | 1.12 ± 0.04 | 17.6 ± 0.9 | 0.76 ± 0.01 |
| S33 | 1.05 ± 0.04 | 21.3 ± 0.9 | 0.82 ± 0.07 |
| I34 | 1.13 ± 0.05 | 16.8 ± 1.2 | 0.90 ± 0.06 |
| I40 | 1.08 ± 0.03 | 15.5 ± 0.9 | 0.85 ± 0.02 |
| G42 | 0.96 ± 0.04 | 14.2 ± 1.3 | 0.68 ± 0.07 |
| G43 | 0.99 ± 0.02 | 19.2 ± 0.8 | 0.77 ± 0.02 |
| A46 | 1.05 ± 0.02 | 19.0 ± 0.6 | 0.80 ± 0.04 |
| Q47 | 0.88 ± 0.03 | 17.1 ± 0.4 | 0.84 ± 0.00 |
| G49 | 1.07 ± 0.03 | 16.7 ± 0.8 | 0.86 ± 0.02 |
| R50 | 1.03 ± 0.01 | 18.1 ± 0.4 | 0.82 ± 0.03 |
| L51 | 1.02 ± 0.05 | 18.3 ± 0.7 | 0.68 ± 0.00 |
| L58 | 1.16 ± 0.04 | 16.0 ± 1.1 | 0.84 ± 0.02 |
| N61 | 1.07 ± 0.03 | 25.9 ± 0.9 | 0.62 ± 0.01 |
| D64 | 1.01 ± 0.02 | 17.2 ± 0.6 | 0.87 ± 0.05 |
| V65 | 1.07 ± 0.02 | 16.1 ± 0.5 | 0.76 ± 0.02 |
| E67 | 1.02 ± 0.01 | 16.1 ± 0.4 | 0.75 ± 0.02 |

TABLE 3-continued $^{15}$N $R_1$ and $R_2$ relaxation rates and $^1$H-$^{15}$N NOE measured for [$^{15}$N]-PSD95 PDZ1-2 in complex with AB125. Only results for residues where the assignments could be transferred with confidence from Wang et al., J. Am. Chem. Soc. 131, 787, 2009 are shown.

| Residue | $R_1$ (s$^{-1}$) | $R_2$ (s$^{-1}$) | NOE |
|---|---|---|---|
| V68 | 1.04 ± 0.04 | 17.4 ± 0.6 | 0.77 ± 0.00 |
| T69 | 0.95 ± 0.02 | 17.0 ± 0.4 | 0.92 ± 0.03 |
| H70 | 1.07 ± 0.05 | 15.5 ± 1.0 | 0.56 ± 0.12 |
| S71 | 1.06 ± 0.02 | 16.2 ± 0.5 | 0.80 ± 0.03 |
| A72 | 1.10 ± 0.02 | 18.9 ± 0.7 | 0.77 ± 0.04 |
| A73 | 1.12 ± 0.03 | 17.3 ± 0.6 | 0.76 ± 0.07 |
| V74 | 1.07 ± 0.02 | 15.1 ± 0.5 | 0.65 ± 0.02 |
| L77 | 1.01 ± 0.03 | 15.8 ± 0.5 | 0.73 ± 0.03 |
| E79 | 1.01 ± 0.02 | 16.2 ± 0.7 | 0.69 ± 0.05 |
| A80 | 1.02 ± 0.01 | 18.0 ± 0.4 | 0.57 ± 0.01 |
| G81 | 1.13 ± 0.03 | 16.0 ± 1.1 | 0.68 ± 0.00 |
| I83 | 1.04 ± 0.02 | 16.6 ± 0.6 | 0.72 ± 0.02 |
| V84 | 1.08 ± 0.02 | 15.9 ± 0.6 | 0.71 ± 0.01 |
| R85 | 1.02 ± 0.03 | 19.7 ± 1.0 | 0.88 ± 0.04 |
| L86 | 1.17 ± 0.03 | 15.9 ± 0.7 | 0.64 ± 0.07 |
| M99 | 1.23 ± 0.04 | 16.0 ± 1.2 | 0.57 ± 0.01 |
| K102 | 1.05 ± 0.03 | 13.5 ± 0.7 | 0.74 ± 0.02 |
| I104 | 1.09 ± 0.02 | 13.8 ± 0.3 | 0.61 ± 0.03 |
| K105 | 1.23 ± 0.02 | 14.2 ± 0.5 | 0.69 ± 0.03 |
| G106 | 1.05 ± 0.03 | 14.6 ± 0.7 | 0.60 ± 0.01 |
| G109 | 0.99 ± 0.02 | 15.3 ± 0.5 | 0.47 ± 0.01 |
| G111 | 1.18 ± 0.02 | 15.9 ± 0.6 | 0.81 ± 0.01 |
| F112 | 1.18 ± 0.01 | 15.6 ± 0.6 | 0.88 ± 0.01 |
| G119 | 1.11 ± 0.04 | 16.5 ± 0.9 | 0.87 ± 0.07 |
| Q121 | 1.09 ± 0.03 | 15.8 ± 0.7 | 0.85 ± 0.03 |
| H122 | 1.04 ± 0.03 | 17.6 ± 0.5 | 0.73 ± 0.02 |
| I123 | 1.05 ± 0.05 | 12.8 ± 1.5 | 0.64 ± 0.09 |
| G125 | 1.11 ± 0.06 | 12.9 ± 0.5 | 0.70 ± 0.09 |
| N127 | 1.12 ± 0.03 | 15.8 ± 1.6 | 0.64 ± 0.01 |
| S128 | 1.00 ± 0.03 | 19.1 ± 0.6 | 0.75 ± 0.01 |
| I135 | 1.18 ± 0.03 | 15.4 ± 0.8 | 0.69 ± 0.03 |
| E136 | 1.12 ± 0.06 | 18.7 ± 1.0 | 0.72 ± 0.04 |
| G137 | 1.06 ± 0.05 | 13.9 ± 1.2 | 1.27 ± 0.14 |
| G138 | 1.06 ± 0.03 | 17.3 ± 0.6 | 0.67 ± 0.02 |
| H141 | 1.27 ± 0.04 | 17.0 ± 1.4 | 0.69 ± 0.02 |
| K142 | 1.11 ± 0.04 | 13.5 ± 0.7 | 0.71 ± 0.01 |
| D143 | 1.16 ± 0.02 | 14.4 ± 0.5 | 0.90 ± 0.02 |
| G144 | 1.02 ± 0.02 | 14.5 ± 1.2 | 0.82 ± 0.00 |
| I148 | 1.11 ± 0.03 | 16.1 ± 0.4 | 0.70 ± 0.04 |
| G149 | 1.10 ± 0.03 | 18.2 ± 0.8 | 0.74 ± 0.03 |
| D150 | 1.15 ± 0.02 | 18.1 ± 0.5 | 0.81 ± 0.02 |
| L153 | 1.12 ± 0.03 | 15.3 ± 0.9 | 0.76 ± 0.00 |
| V155 | 1.14 ± 0.04 | 16.7 ± 0.5 | 0.68 ± 0.01 |
| N156 | 1.19 ± 0.03 | 17.0 ± 0.7 | 0.76 ± 0.09 |
| E166 | 1.03 ± 0.02 | 17.8 ± 0.5 | 0.74 ± 0.06 |
| A168 | 1.00 ± 0.02 | 18.0 ± 0.4 | 0.71 ± 0.01 |
| V169 | 1.02 ± 0.02 | 19.3 ± 0.6 | 0.75 ± 0.10 |
| L172 | 1.03 ± 0.02 | 16.2 ± 0.6 | 0.63 ± 0.03 |
| T175 | 1.05 ± 0.03 | 9.0 ± 0.4 | 0.40 ± 0.00 |
| V178 | 1.02 ± 0.02 | 13.2 ± 0.3 | 0.68 ± 0.02 |
| V179 | 1.12 ± 0.02 | 15.2 ± 0.7 | 0.71 ± 0.10 |
| L181 | 1.06 ± 0.03 | 15.3 ± 0.6 | 0.93 ± 0.04 |

Example 8

CPP-containing Dimeric PSD-95 Inhibitors Cross the Blood-brain Barrier 8.1 Blood-brain Barrier (BBB) Permeability Analysis These fluorescent labeled ligands were used as surrogate measurements for the ability of CPP-containing dimeric PSD-95 inhibitors to cross the blood-brain barrier and enter the brain in mice. The fluorescent ligands were injected intravenously (3 nmol/g) and the location of the ligands was detected by fluorescence microscopy of coronal brain slices (n=8) mice, was evaluated 2 hours after injection. Two sections of the brain, prior to and two after the anterior commissure (n=5), were selected for BBB permeability analysis. The anterior commissure (Bregma: −0.3) was used as a fix point in the brain in order to analyse anatomically identical brain sections. The intensity of the 5-FAM fluorophore was measured semi-quantitatively using a fluorescence microscopy system (Olympus System Microscope model BX-51, Denmark) with a 10× objective (Olympus 10×/0.15 UPlanApo) connected to a high-resolution microscope digital camera (Olympus model DP70), which transferred images to an image-capturing software (Image Pro Plus software). All images were taken using the same microscope settings and with constant camera exposure time. Intensities were quantified using the ImageJ software.

8.2 Blood-brain Barrier (BBB) Permeability of CPP-dimeric PSD-95 Inhibitors

Figure 8:
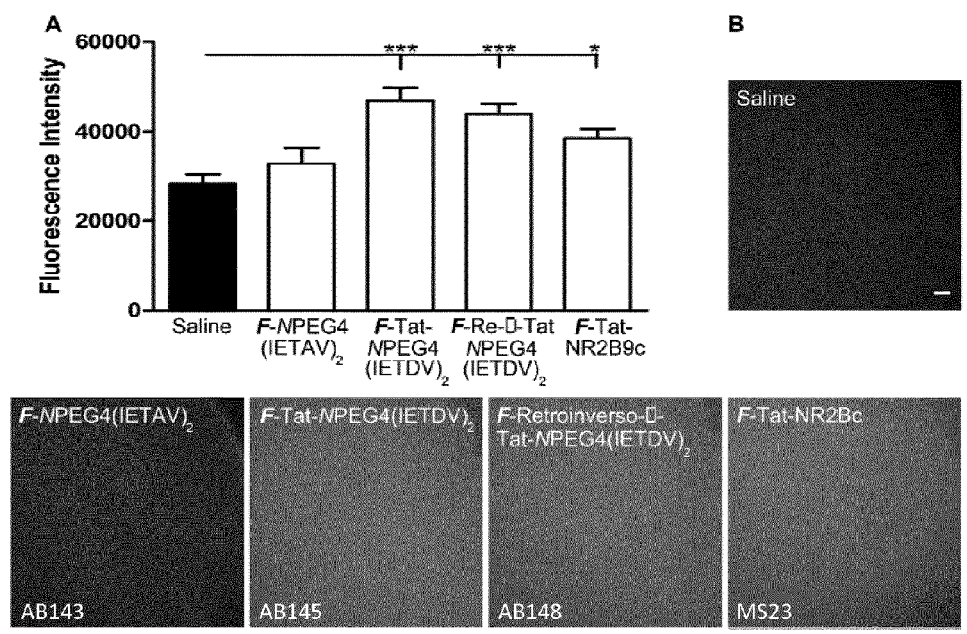
FIG. 8. Blood-brain barrier permeability of fluorescent analogues in unmanipulated mice. (A) Bar graph of the mean fluorescence intensity of 5-FAM (F)-labeled compounds, 2 hours after intravenous (i.v.) injection as compared to saline treated mice. (B) Detection of F-Tat-NPEG4(IETDV)$_2$ (SEQ ID NO: 18) (AB145) (n=2), F-Retroinverso-D-Tat-NPEG4 (IETDV)$_2$ (SEQ ID NO: 18) (AB148) (n=2), and F-Tat-NR2B9c (MS23) (n=2) but not F-NPEG4(IETAV)$_2$ (SEQ ID NO: 16) (AB143) (n=2), as compared to saline mice (n=2). F=5-FAM; Re=Retroinverso. Data are presented as mean±SEM; *//*: p<0.05/0.01/0.001 (non-parametric Mann-Whitney). Scale bar: 100 μm.

The dimeric PSD-95 inhibitors AB143, AB145, AB148 are the 5-FAM-labeled derivatives of AB141, AB144, AB147, respectively (FIG. 4: AB143 and AB145 are shown as examples). 5-FAM-labeled derivative of Tat-NR2B9c is designated MS23. After injection of the compounds, the mice are perfused with paraformaldehyde and the brains are carefully removed, post-fixed in paraformaldehyde, processed into coronal sections, and quantified for fluorescence. Fluorescence microscopy of coronal brain slices showed that AB145, AB148, and Tat-NR2B9c enter the brain, while AB143 does not (FIG. 8). Based on these results it is concluded that compounds containing Tat or Retroinverso-D-Tat (AB144, AB147, Tat-NR2B9c) are able to enter the brain, while AB125/AB141, which do not contain a CPP, cannot.

Example 9

Neuroprotective Properties of CPP-dimeric PSD-95 Inhibitors Reduces Infarct Volumes in Mice with Focal Cerebral Ischemia The in vivo neuroprotective properties of CPP-containing dimeric PSD-95 inhibitors, were examined in the permanent middle cerebral artery occlusion (pMCAO) model of ischemic stroke in mice.

9.1 Mice for In Vivo Studies

The pMCAO study was performed using 164 age-matched, young adult (7-8 weeks), male C57BL/6 mice (Taconic, Denmark). The mice were housed in separate cages under diurnal lightning and given free access to food (1314 Altromin, Brogården, Denmark) and water. Mice acclimatized for 7 days prior to surgery in accordance with guidelines approved by the Danish Animal Ethical Committee (J. no. 2005/561-1068). The extent of the ischemic infarct was measured in two randomized, double-blinded, placebo controlled studies 9.2 Permanent Middle Cerebral Artery Occlusion Surgical procedure: Mice were subjected to focal cerebral ischemic by permanent occlusion of the middle cerebral artery (pMCAO). Mice were anesthetized by subcutaneous injections of 0.18 mL per 10 gram body weight, of a 1:1:2 mixture of Hypnorm™ (fentanyl citrate 0.315 mg/mL and fluanisone 10 mg/mL, VectaPharma Ltd), Midazolam (5 mg/mL, Hameln), and distilled $H_2O$. The mouse was placed on a 37±0.5° C. heating pad and the eyes coated with ointment (Viscotears; Novartis, Basel, Switzerland). A skin incision was made between the lateral part of the orbit and the external auditory meatus. The superior pole of the parotic gland and the upper part of the temporal muscle were pushed aside after partial resection and a small craniotomy, using a 0.8 mm burr was made directly above the distal branch of the MCA. The dura mater was removed and the MCA electrocoagulated using bipolar forceps (Gimmi, Germany) coupled to an electrosurgical unit (ICC50 from ERBE, Germany). Following occlusion, the muscle and soft tissue were organized and the skin sutured using a 4-0 nylon suture. For post-surgical pain treatment the mice were supplied with Temgesic (0.001 mg/20 g buprenorphinum, Reckitt & Coleman, UK), three times with an 8 hour interval starting immediately after surgery. In addition, the mice were injected s.c. with 1 ml of isotonic saline before transfer to a 28° C. controlled recovery room.

9.3 Compound Administration

Compounds were dissolved in isotonic (0.9%) saline (NaCl) to a concentration of 300 µM, and 10 µl per gram body weight was administered intravenously (i.v.) (Dose: 3 nmol/g) as a bolus, into the tail, 30 min after surgery. Control mice received an i.v. injection of 0.9% NaCl.

9.4 Termination of the Mice and Brain Tissue Processing

C57BL/6 mice with 6 hour post-surgical survival time were euthanized by cervical dislocation. C57BL/6 mice with 48 hour post-surgical survival were anesthetized with an overdosed of pentobarbital (the pharmacy of the Faculty of Life Sciences, University of Copenhagen, Denmark) in order to collect blood and tissue samples. All brains were carefully removed, frozen in gaseous $CO_2$ and cut into 6 series of 30 µm coronal cryostat sections and stored at −80° C. until further use. C57BL/6J mice used to investigate the blood-brain barrier (BBB) permeability of AB143, AB145, AB148, and MS23 were deeply anesthetized and perfused through the left ventricle, using 10 ml chilled Soerensens phosphate buffer (SB) (25 nM $KH_2PO_4$, 125 mM $Na_2HPO_4$, pH 7.4) followed by 20 mL SB containing 4% paraformaldehyde (PFA). The brains were carefully removed and post-fixed in 4% PFA for 1 hour followed by immersion in SB containing 20% sucrose over night. The brains were frozen on gaseous $CO_2$ and processed into 16 µm coronal cryostat sections.

9.5 Determination of Infarct Volume

One series of fresh frozen brain sections from each mouse was fixated in 70% ethanol over night at 4° C. Sections were rehydrated and immersed in a toluidine blue solution (0.01%, Merck, Germany) diluted in 80 mmol/L $Na_2HPO_4 \times 2H_2O$ and 70 mmol/L citric acid), followed by rinsing three times in $H_2O$ and dehydrated in graded series of alcohol (96-99% ethanol). The sections were cleared in xylene and cover-slipped in Depex (BDH Gun, UK). Sections were used for infarct volumetric analysis using a Computer Assisted Stereological Test (CAST) GRID microscope-system (Olympus, Denmark) and the Cavalieri principle for volume estimation. The total volume of the infarct (Vtotal) was calculated using the formula: $V_{total} = \Sigma P * t * a_{point}$, where $\Sigma P$ is the total number of points hitting the infarct, t is the mean distance between sections, and $a_{point}$ represents the area per point.

9.6 Statistical Analysis

The statistical analysis was done using the Graphpad Instat 5.0 program for Windows (GraphPad software, San Diego, Calif., USA). Comparison of mean values of infarction sizes between two groups of mice was done using the non-parametric Mann-Whitney test. Two-tailed, paired Student's t test was used to compare grip strength values obtained from the same mouse before and after surgery. Wilcoxon signed-rank test was used on repeated measurements from the same mouse (Rotarod Performance Test). Two-way analysis of variance was used to investigate independent variables (time and weight or temperature). All data are presented as means±SEM. Statistical significance was accepted for $P<0.05$.

Figure 9:
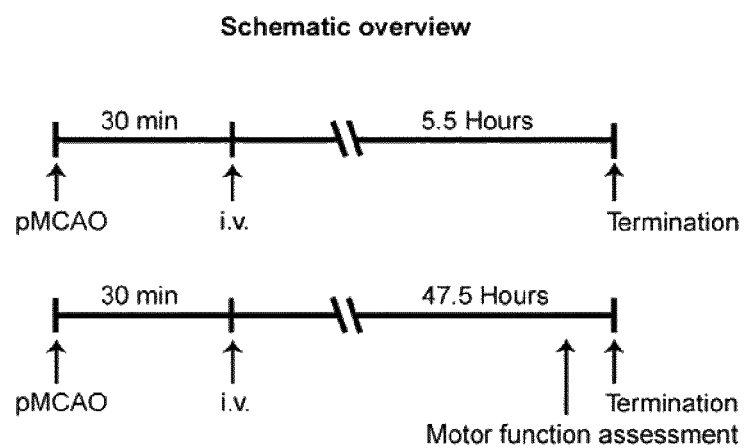
FIG. 9. Time line of pMCAO experiments. All compounds were administered i.v. (3 nmol/g) 30 minutes post-surgery, followed by a survival period of either 5.5 or 47.5 hours.
Figure 10:
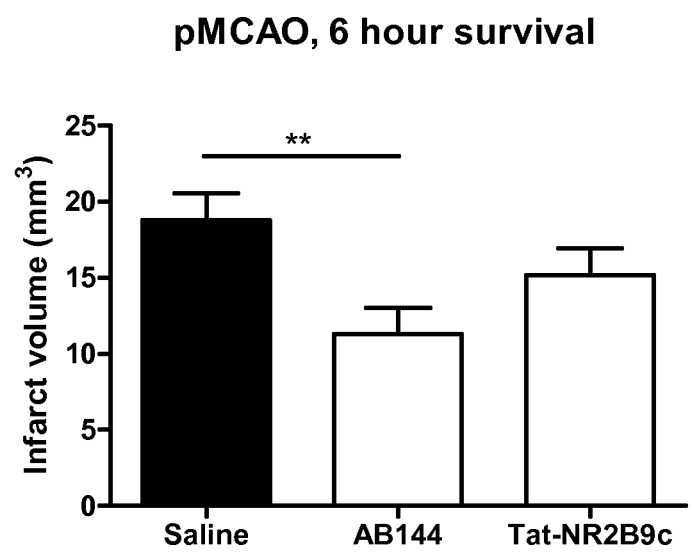
FIG. 10. Neuroprotective effect of compounds after a 6 hour post-surgical survival period. Bar graph showing mean infarct volumes 6 hours after pMCAO. AB144 treatment significantly reduced ischemic brain damage compared to saline treated control mice, an effect which was not achieved by monomeric Tat-NR2B9c treatment (n=16-19). Data are shown as mean±SEM; *//*: p<0.05/0.01/0.001; Nonparametric Mann-Whitney test.

9.7 The Neuroprotective Effects of CPP-containing Dimeric PSD-95 Inhibitors—Short Term The protective effect of AB144 and Tat-NR2B9c was compared to saline in the pMCAO model of cerebral focal ischemia in adult mice (n=60). The inhibitors were intravenously injected (3 nmol/g) 30 minutes after the insult, followed by a 5.5 hour post-surgical survival period (FIG. 9). AB144 showed a significant 40% reduction of the ischemic tissue damage compared to saline treated mice, whereas Tat-NR2B9c did not provide a statistically significant reduction in infarct volumes (FIG. 10). Thus the combination of a remarkable high affinity, due to the dimeric structure, and blood-brain barrier permeability, facilitated by the Tat peptide, leads to the in vivo neuroprotective compound, AB144, with superior activity compared to Tat-NR2B9c.

Figure 11:
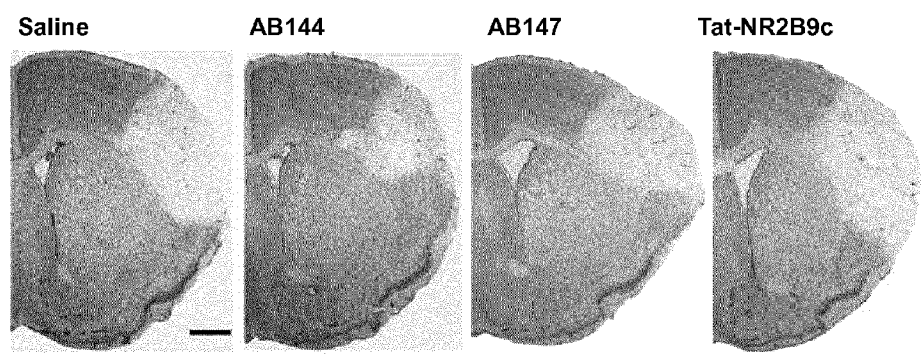
FIG. 11. Neuroprotective effect of compounds after a 48 hour post-surgical survival period. Toluidine blue staining showing the ischemic brain damage 48 hours after pMCAO. Scale bar: 1 mm.
Figure 12:
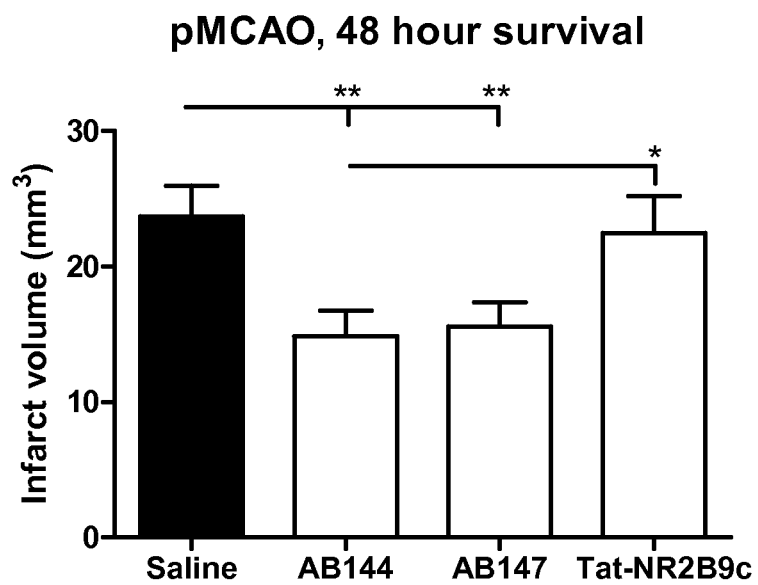
FIG. 12. Neuroprotective effect of compounds after a 48 hour post-surgical survival period. Bar graph showing a longer lasting infarct reducing effect of AB144 compared to saline treated control mice, and significantly smaller infarcts compared to mice treated with the monomeric Tat-NR2B9c (n=16-19). Also, AB147 produced a longer lasting infarct reduction similar to AB144. Data are shown as mean±SEM; *//*: p<0.05/0.01/0.001; Nonparametric Mann-Whitney test.

9.8 The Neuroprotective Effects of CPP-containing Dimeric PSD-95 Inhibitors—Long Term The long-lasting neuroprotective effects of AB144, AB147, and Tat-NR2B9c, as compared to saline, was evaluated 48 hours after pMCAO (n=80) (FIG. 9). AB144 and AB147 provided respectively a 37% and 34% reduction in infarct size compared to saline treated mice, while no statistically significant infarct reduction was detected on treatment with Tat-NR2B9c (FIGS. 11 and 12).

9.9 The Physiological Status of pMCAO Mice

The physiological status of the mice was carefully monitored prior to and during pMCAO surgery in order to exclude the observed effects of treatment with dimeric PSD-95 inhibitors being due to secondary conditions (e.g. disease-related) resulting from the experimental procedure.

Figure 13:
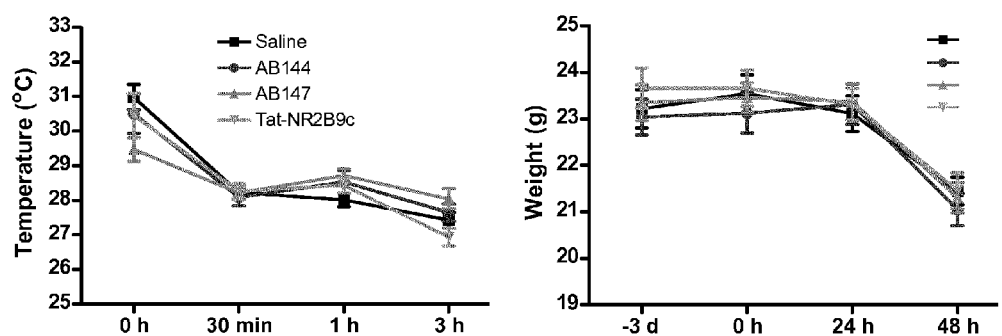
FIG. 13. Physiological parameters such as (left) temperature and (right) body weight were registered prior to and after pMCAO (48 hour experiment). Time points (x-axis) indicate time relative to surgery (0 h). (Left) Graph showing an anesthesia-induced drop in body temperature, 30 min after pMCAO, which however was registered prior to i.v. injections. No drug-induced differences were registered among groups 1 and 3 hours after surgery. (Right) Graph showing no difference in body weight among groups, 3 days prior to and 24 hours and 48 hours after pMCAO (0 h). Data shown as mean±SEM. Two-way Anova.

9.10 Body weight monitoring: The body weight of each mouse was registered during pre-training, before surgery, and at 24 and 48 hours after surgery and no differences were seen between the treatment groups (FIG. 13).

9.11 Temperature monitoring: The rectal temperature of the mouse was continuously measured using a thermocoupled probe connected to a Model Bat 12 unit (Physitemp). The temperature was measured prior to and 30 min after pMCAO in addition to 30 min and 2.5 hours after i.v. injection, i.e. 1 and 3 hours after pMCAO. No differences were seen in body weight (FIG. 13) or survival rates (>96%), after drug injection compared to saline treated mice.

9.12 Blood gas analysis: One samples of venous blood was taken for blood gas analysis of $PO_2/PCO_2$ electrolytes, glucose, lactate, and hematocrit, 30 min after compound administration (1 hour after pMCAO). A capillary heparin coated tube was inserted along the inner corner of eye and turned until it penetrated the conjunctiva. A sample of blood (150 µl) was collected and stored on ice until gas analysis using the GEM Premier 300 blood gas instrument (Instrumentation Laboratory) Quality controls (QC ContrlIL9) were purchased from IL Sensor Systems. Also, no differences were detected in blood gas parameters ($PO_2/PCO_2$, pH, electrolytes, glu/lac), which were similar between the groups and within normal range, when compared to unmanipulated control mice (Table 4).

Example 10

Neuroprotective Properties of CPP-dimeric PSD-95 Inhibitors Conserves Motor Function in Mice with Focal Cerebral Ischemia The mice with 48 hours post-surgical survival in the (pMCAO) model of ischemic stroke (Example 9) were examined using the three following behavioral tests in order to detect motor deficits that may not necessarily manifest in the infarct size, thereby giving a more general impression of the animal's condition.

10.1 Grip Strength

The grip strength meter (BIO-GT-3, BIOSEB) allows the study of neuromuscular functions in mice by determining the maximum force that is required to make the mouse release its grip. The grip strength in individual paws was used to measure the severity of the pMCAO-induced asymmetry. The mouse is allowed to grasp a metal grid and then pulled backwards in the horizontal plane. The force applied to the grid is recorded as the peak tension. The strength of individual front paws and the total grip strength (both paws simultaneously) were measured before (baseline) and after pMCAO. Each mouse is tested in 5 sequential trials and the highest grip strength is recorded as the best score.

10.2 Rotarod Performance Test

The rotarod (LE 8200, Panlab) is well suited to evaluate motor activity in rodents, experimental compound effects on central nervous system damage, or disease effects on motor coordination, assessed by the time during which the animal remains walking in a rotating drum. The rotation of the rotarod is motor drived and accelerates from 0 to 40 rounds per min (rpm) over a time period of 5 min, at which time all mice have fallen off the rod. All mice were tested in 4 repeating trials with a 20 min interval (resting time). Prior to surgery mice were pre-trained to stay on the rod for 30 seconds, at 4 rpm.

Figure 14:
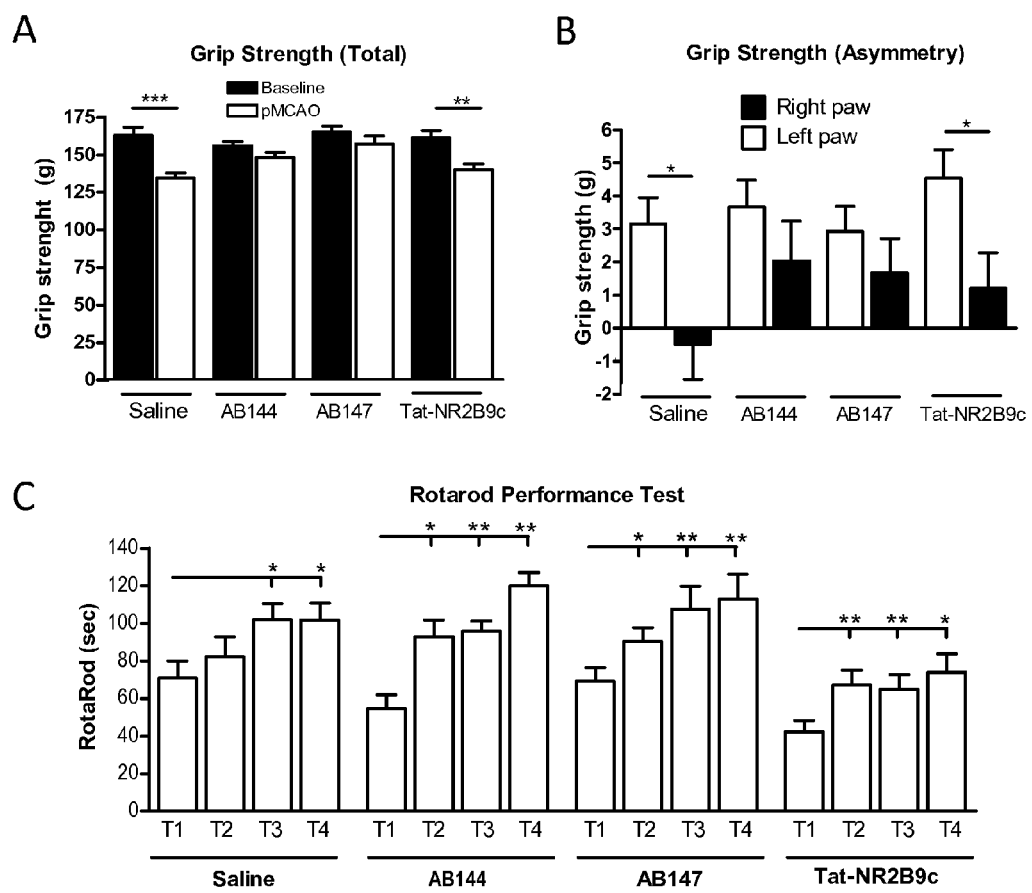
FIG. 14. Motor function assessment of mice with 48 hours post-surgical survival. (A) Bar graph showing the mean grip strength of both front paws before (baseline) and after pMCAO. Saline and Tat-NR2B9c treated mice showed significant reduced grip strength when compared to baseline, 48 hours after pMCAO. No difference compared to baseline was observed in mice treated with AB144 and AB147. (B) Bar graph showing the ischemia-induced asymmetry in the front paws, here observed in both saline and monomeric Tat-NR2B9c treated mice, however not in AB144 and AB147 treated mice. (C) Rotarod performance test of four trials (T1-T4), showing the short term motor learning skills of mice 48 hours after pMCAO. Data, reveal a learning component along the trials in all groups of mice, however treatment with AB144 and AB147 gave a more pronounced improvement (cf. T2) compared to saline, and increased endurance compared to Tat-NR2B9c (See text). (A-C) All data are shown as mean±SEM; *//*: p<0.05/0.01/0.001; (A-B) Paired Student's t test; (C) Wilcoxon matched pairs test.

10.3 The Neuroprotective Effect of CPP-containing Dimeric PSD-95 Inhibitors Preserves Grip Strength and Motor Coordination pMCAO mice treated with either AB144 and AB147 showed no significant change in total grip strength (both paws), while mice treated with saline or Tat-NR2B9c lost a significant amount of grip strength (FIG. 14A). Similarly,

TABLE 4

Blood values were monitored during the pMCAO (48 hour survival period) experiment at 1 hour after surgery.

| Value | Control | Saline | AB144 | AB147 | Tat-NR2B9c |
|---|---|---|---|---|---|
| pH | 7.19 ± 0.03 | 7.17 ± 0.01 | 7.16 ± 0.01 | 7.13 ± 0.01 | 7.13 ± 0.01 |
| pCO2 (mmHg) | 88.4 ± 2.7 | 101 ± 2.7 | 95.7 ± 2.3 | 104 ± 2.5 | 106 ± 2.4 |
| pO2 (mmHg) | 47.6 ± 3.4 | 54.0 ± 1.6 | 50.2 ± 2.2 | 56.4 ± 2.9 | 55.2 ± 2.6 |
| [Na$^+$] (mmol/L) | 145 ± 0.3 | 147 ± 0.6 | 148 ± 2.0 | 147 ± 0.5 | 147 ± 0.3 |
| [K$^+$] (mmol/L) | 5.6 ± 0.21 | 4.8 ± 0.09 | 5.2 ± 0.20 | 5.1 ± 0.18 | 5.1 ± 0.13 |
| [Ca$^{2+}$] (mmol/L) | 1.29 ± 0.01 | 1.32 ± 0.01 | 1.30 ± 0.02 | 1.31 ± 0.01 | 1.32 ± 0.01 |
| [Glucose] (mmol/L) | 139 ± 4.5 | 146 ± 6.2 | 134 ± 7.9 | 154 ± 8.1 | 141 ± 7.4 |
| [Lactate] (mmol/L) | 0.99 ± 0.04 | 0.90 ± 0.06 | 0.93 ± 0.07 | 0.90 ± 0.05 | 0.87 ± 0.07 |
| Hct (%) | 42.8 ± 0.4 | 42.0 ± 0.5 | 43.5 ± 0.9 | 41.3 ± 0.6 | 40.8 ± 0.6 |

Values are shown as mean ± SEM.
'Control' indicates unmanipulated animals.

grip strength analysis showed no asymmetry between the right and left front paw for AB144 and AB147 treated mice compared to mice treated with saline and Tat-NR2B9c (FIG. 14B), which clearly demonstrates the neuroprotective effect of AB144 and AB147. In the rotarod performance test, AB144 and AB147 treated mice showed both a more pronounced short term learning skill improvement than saline treated mice (FIG. 14C), and the total time the mice spend on the rod was significantly longer (AB144: 83.5±4.1 seconds; AB147: 92.6±4.5 seconds) than for mice treated with Tat-NR2B9c (65.7±3.6 seconds) ($P<0.001$).

Example 11

Dimeric PSD-95 Inhibitors Alleviates Inflammatory Pain Conditions 11.1 Animals

Female NMRI mice (22-26 grams) obtained from Taconic M&B (Ry, Denmark) were used for all experiments and were 8-9 weeks of age at the time of testing. After arrival, mice were allowed a minimum of 7 days acclimatisation in Macrolon III cages (20×40×18 cm) with 7 mice per cage. Food and water was available ad libitum on a 12/12 h light/dark cycle with lights on at 6 am. Experiments were performed between 9:00 am and 16.00 pm in temperature and humidity-regulated rooms (22-24° C., relative humidity: 60-70%). All testing procedures were in accordance with "Principles of Laboratory Animal Care" (NIH publication No. 85-23, revised 1985) and the Danish Animal Experimentation Act, and all efforts were made to minimise animal suffering.

11.2 Induction of Inflammatory Pain by Complete Freund's Adjuvant and Compound Administration Persistent inflammatory pain was induced by subcutaneous (s.c.) injection of 20 μl of Complete Freunds Adjuvant suspension (CFA; 1 mg/ml *Mycobacterium tuberculosis*; Sigma-Aldrich, Saint Louis, USA) into the plantar surface of the left hind-paw, using a GASTIGHT® 50 μl microsyringe (Hamilton Company) with a 30 1/2-gauge needle. Baseline measurements of withdrawal threshold to mechanical stimuli were performed once daily, three times prior to CFA injection. Vehicle (0.9% saline) or AB125 (3, 10, or 30 mg/kg) were given intraperitoneally in an injection volume of 10 ml/kg (AB125 dissolved in 0.9% saline). CFA and vehicle/AB125 were administered at least 24 hours prior to testing of mechanical sensitivity.

11.3 Pain Test—the Von Frey Test for Mechanical Allodynia/Hyperalgesia Induced by CFA To assess the degree of hyperalgesia/allodynia induced by CFA treatment the 50% paw withdrawal threshold (PWT) to mechanical stimuli was measured by using the up-and-down method (Chaplan et al., J Neuroscience Methods, 1994, 53, 55-63). Briefly, mice were placed individually in transparent dark red plastic box on the metal wire mesh floor for at least 30 min to adapt to the environment. A series of von Frey filaments (Stoelting, Wood Dale, Ill.) with bending forces equivalent to 0.008, 0.02, 0.04, 0.07, 0.16, 0.40, 0.60, 1.00, and 1.4 grams were used to deliver the stimuli. Beginning with filament 0.6, the von Frey filaments were applied perpendicularly to the plantar surface of the hind paws for 4-5 s. When a positive response to a stimulus occurred, the next smaller von Frey filament was applied. When a negative response occurred, the next higher filament was used. The pattern of positive and negative responses was converted to 50% threshold (Chaplan et al., J Neuroscience Methods, 1994, 53, 55-63), which was expressed as gram (g) values according to the following formula: $50\% \ PWT = 10^{(G+0.2237*K)}$, where G is the bending force of the last von Frey filament and K is the value obtained from the standardized table based on the up-and-down pattern. Lifting the paw due to normal motor behavior was ignored, and testing during deep sleep, grooming and exploring was avoided. Treatment was blinded to the test person.

11.4 Social Transmission of Food Preference Test

STFP was conducted in two phases. First phase: a 'demonstrator' mouse from each cage of 4 food-deprived mice was transferred to a separate cage and allowed to eat for 30 min from crushed food mixed with either 1% cinnamon or 2% cocoa powder. Then the 'demonstrator' mice were brought back to their respective home cages for 30 minutes. During this 'presentation phase' the number of interactions between the three 'observer' mice and the demonstrator mice was scored. A minimum of 2 and a maximum of 5 licking/sniffing interactions were set as criteria for appropriate acquisition of the odour cue. After this first phase, the 'demonstrator' mouse was removed and the three 'observer' mice were transferred to a clean cage with free access to food and water for 4 hours before the food deprivation preparing them for the second phase. Second phase: following a 24-hour retention interval, the observer mice were placed individually in cages containing two trays of crushed food scented with cinnamon or cocoa, respectively. The amount eaten from the cued food over the novel food is taken as an index of memory for the previously cued food. Pilot studies have shown that mice do not show any inherent preference when given a choice between cinnamon- and cocoa-scented food. Yet, experiments were designed in a balanced fashion to ensure that an equal number of mice within each treatment group were cued with cinnamon and cocoa, respectively.

11.5 Modified Y-maze

Testing was carried out in a clear Plexiglass maze composed of 2 perpendicular arms connected to a runway. The 2 arms (available for exploration) and runway were 50 cm long and 8 cm wide, surrounded by clear Plexi-glass walls 30 cm high. Each arm met at a central platform equipped with black removable partitions, enabling arms to be opened and closed as desired. The whole maze was enclosed in a triangular black Plexiglass box (1×1×1 m). The walls of this outer box surrounding each exploration arm were covered with distinct optical cues, e.g., white horizontal or vertical lines. The area surrounding the runway did not contain optical cues and was black in colour. Each arm of the maze was separated from another by an opaque partition, so a mouse on entering an arm could only see the distinct optical cues of that particular arm. The test consisted of two phases: In phase 1 (habituation), the mouse (n=8-10) was placed at the end of the runway and was allowed access to one of the exploration arms by forced choice (i.e., the other arm was closed). After the mouse had entered the arm, access to the runway was blocked, and the mouse was allowed to explore the arm (termed familiar) for a period of 5 min. The familiar arm was alternated systematically to eliminate any place preference to confound the assay. Immediately thereafter, in phase 2 (testing), the mouse was allowed to explore both the familiar and the unfamiliar exploration arms, but not the runway, for a period of 2 min. The cumulative time spent in each arm was recorded during this test session by an automated video tracking system (Ethovision, Noldus). A discrimination index (DI) was calculated for each mouse, defined as the difference in time spent in the novel and the familiar arm divided by the total time spent in the novel and the familiar arm during phase 2 testing, i.e. DI=(novel−familiar)/(novel+familiar).

11.6 Rotarod Test

Motor function was evaluated using an accelerating rotarod (MedAssociates, Inc., VT, USA). The rotarod (3.2 cm diameter) speed was increased from 4 to 40 rpm over a 300 s period with the minimum time possible to spend on the rod designated as 0 s and the maximum cut-off time set at 310 s. Each mouse was tested immediately prior to drug treatment (t=0), and again 15, 30, 45 and 60 minutes after drug treatment. When an animal fell off the rotating drum, a photobeam was automatically broken to record the amount of time spent on the rotating rod.

11.7 Data Analysis

Pain data: Baseline mechanical threshold was defined as the average of von Frey measurements taken on the three consecutive days prior to CFA treatment, with the last baseline measurement taken on the same day as the CFA treatment. Statistical analysis was performed using two-way repeated measures analysis of covariance (RM-ANCOVA), with Treatment as the independent factor, Time as the repeated factor, and baseline mechanical threshold as the covariate. The RM-ANCOVA was followed by Planned Comparisons on the predicted means to assess the effect of the treatments over time on the threshold sensitivity. The analysis was performed on the raw data, while the results are depicted as relative values (e.g. baseline defined as 1).

Cognitive data: In the social transmission of food preference test, the preference for the cued food was expressed as a discrimination index, DI=(cued−novel)/(cued+novel). In the modified Y-maze, the preference for the novel arm was expressed as a discrimination index, DI=(time in novel−time in familiar)/(time in novel+time in familiar). STFP and Y-maze data were analysed by one-way ANOVA followed by Planned Comparisons was performed to assess treatment effects on the discrimination index.

Motor performance: In the rotarod test, treatment effect on motor coordination was analysed using a two-way RM ANOVA, with treatment as the independent factor and time as repeated measure. Planned comparisons procedure was used to assess treatment effects over time.

11.8 AB125 Reduces Mechanical Allodynia/Hyperalgesia Induced by CFA

AB125 reduces CFA-induced pain response when injected intraperitoneally at both 3, 10 and 30 mg/kg (FIG. 17). This is shown by injecting CFA and AB125 simultaneously into the mice, and measuring mechanical allodynia/hyperalgesia 24 hours afterwards. This result illustrates that PSD-95 inhibitors, without a CPP attached, are efficient analgesics against inflammatory (CFA-induced) mechanical pain, and therefore promising agents in treatment of chronic pain conditions.

11.9 Analgesic Effects of AB125 Compared to MK-801 in the CFA Pain Model

When administered concurrently with CFA, both the classical NMDA receptor antagonist MK-801 and AB125 prevented the development of CFA-induced mechanical hyperalgesia 1 hour and 24 hours after treatment (FIG. 18).

Figure 19:
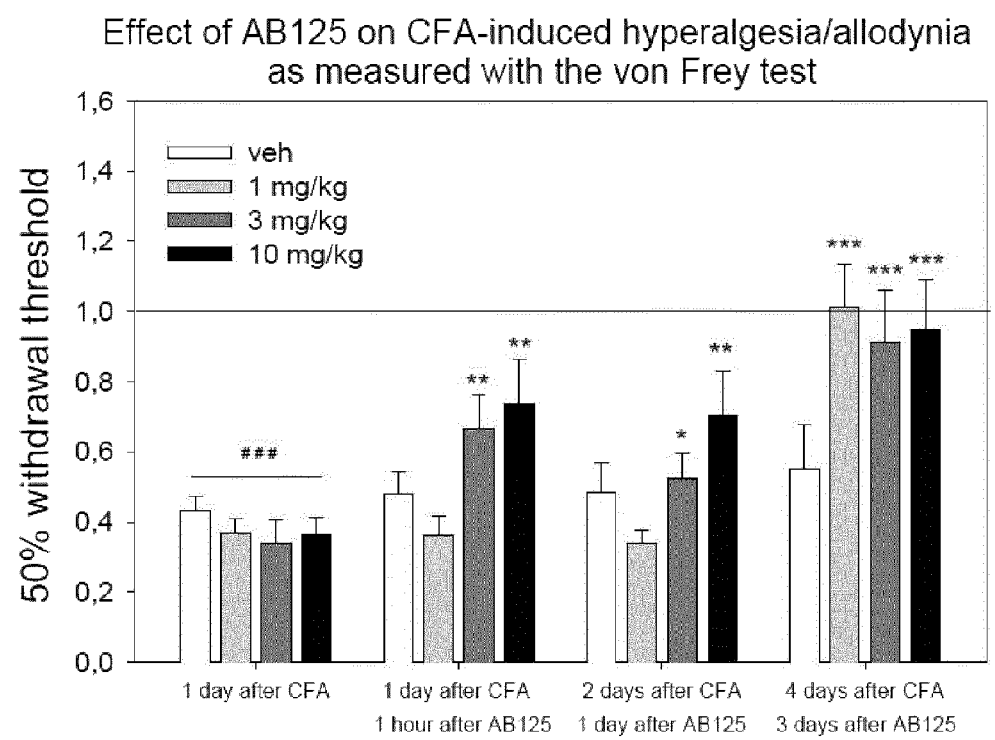
FIG. 19. The effect of AB125 when given 24 hours after CFA-injection. The ANCOVA revealed a significant main effect of baseline (F1,34=15,67; p<0.001), a significant main effect of treatment (F4,34=7.98; p<0.001), a significant main effect of time (F2,70=24.41; p<0.001), but no significant treatment by time interaction (F1,70=1.31; p=0.253). Planned Comparisons revealed a reversal of the CFA-induced hyperalgesia by 3 mg/kg (p=0.002) and 10 mg/kg (p=0.001) after 1 hour. A significant reversal was still observed after 24 hours in the 3 mg/kg (p=0.015) and 10 mg/kg (p<0.001) treated groups. At 72 hours, the hyperalgesia was significantly reversed by all doses (1, 3, and 10 mg/kg) (p<0.001).

11.10 Prolonged Analgesic Effects of AB125 when Given 24 Hours after CFA-injection When AB125 was given 24 hours after CFA-injection, the ANCOVA-test revealed a significant reversal of the CFA-induced hyperalgesia at 3 and 10 mg/kg after 1 hour. Moreover, this reversal was still observed after 24 hours in both the 3 mg/kg and 10 mg/kg treated groups; and at 72 hours, the hyperalgesia was significantly reversed by all doses (1, 3, and 10 mg/kg) (FIG. 19). An additional measurement was made 8 days after AB125 treatment, but at this time-point the saline-treated animals had spontaneously recovered to baseline level, precluding the detection of a potentially analgesic effect of AB125.

11.11 Test of AB125 and MK-801 in Cognition and Motor Function Behavioural Tests.

Figure 20:
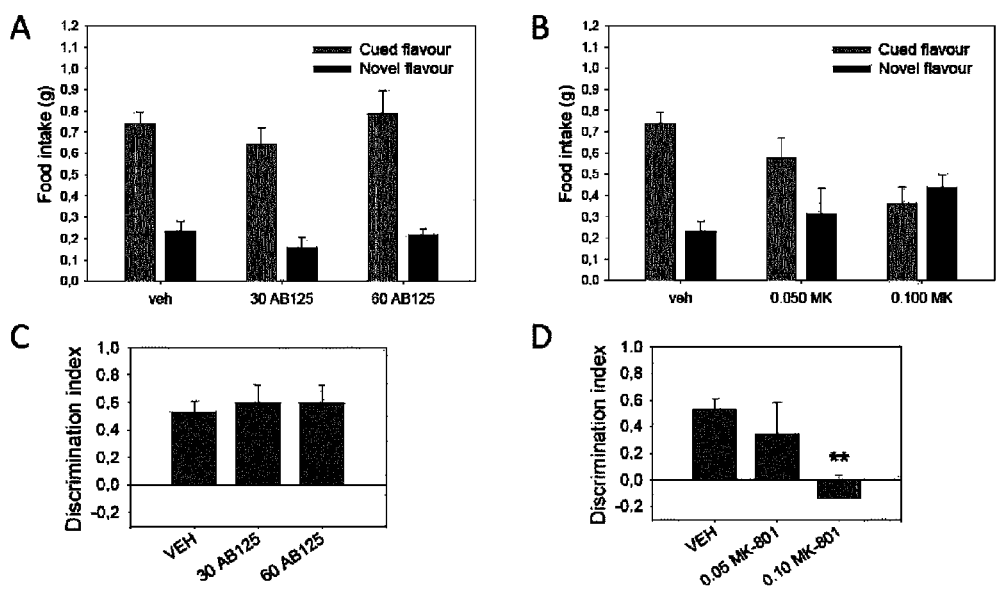
FIG. 20. The effect of AB125 and MK-801 on food intake (a-b) and discrimination index (c-d) in the social transmission of food preference test for long-term reference memory. For AB125, the one-way ANOVA on the discrimination index revealed no significant main effect of treatment (F2, 22=0.108; p=0.898). Planned Comparisons showed no significant effect of the AB125 doses tested (30 and 60 mg/kg shown). For MK-801, the one-way ANOVA revealed a significant main effect of treatment (F2,21=5.28; p=0.014). Planned Comparisons on the predicted mean revealed that 0.1 mg/kg MK-801 significantly reduced the discrimination index (p=0.005).
Figure 21:
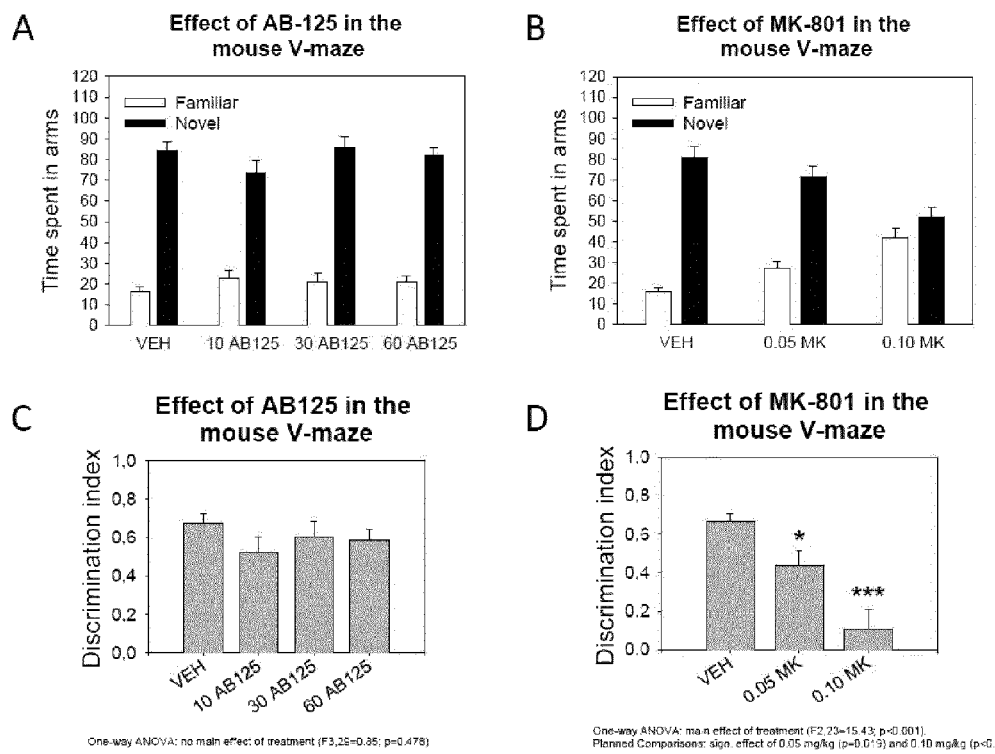
FIG. 21. The effect of AB125 and MK-801 on time spent in the familiar and novel arm in the modified Y-maze (a-b), and on the discrimination index, DI=(novel−familiar)/(novel+familiar) (c-d). For AB125, the one-way ANOVA revealed no significant main effect of AB125 on discrimination index (F3,29=0.85; p=0.478). Planned Comparisons showed no significant effect of the AB125 doses tested (30 and 60 mg/kg shown). For MK-801, the one-way ANOVA revealed a significant effect of treatment (F3,23=15.43; p<0.001). Planned Comparisons revealed that the discrimination index was reduced by both 0.05 (p=0.019) and 0.1 mg/kg MK-801 (p<0.001).

To examine side-effect profiles we compared the effects of AB125 and MK-801 in the social transmission of food preference (STFP) test of long-term memory, and the modified Y-maze test of attention as well as in the rotarod test of motor performance. At the dose reducing hyperalgesia, MK-801 induced cognitive deficits in the STFP (FIG. 20) and modified Y-maze (FIG. 21) tests as well as motor deficits in the rotarod test (FIG. 22). By contrast, AB125 induced no cognitive or motor function deficits in these tests at analgesic doses, or even at higher doses (up to 60 mg/kg) (FIG. 20-22). Thus, PSD-95 inhibitors in the form of AB125 provide an efficient analgesic effect against inflammatory (CFA-induced) mechanical pain, and furthermore, this is without inducing cognitive or motor function side-effects, as is seen for the classical NMDA receptor antagonist MK-801. Hence, dimeric PSD-95 inhibitors are promising agents in treatment of chronic pain.

11.12 AB144 Reduces Mechanical Allodynia/Hyperalgesia Induced by CFA

AB144 also reduces CFA-induced pain response, as shown by injecting AB144 intraperitoneally and concurrently with the CFA-injection and measuring mechanical allodynia/hyperalgesia 1 and 24 hours afterwards. The statistical ANCOVA-test revealed a significant reversal of the CFA-induced hyperalgesia at the 30 mg/kg-dose after 1 hour and at the 10 and 30 mg/kg-doses after 24 hours (FIG. 23). This result illustrates that PSD-95 inhibitors, with a CPP attached, are efficient analgesics against inflammatory (CFA-induced) mechanical pain, and therefore promising agents in treatment of chronic pain conditions.

Example 12

Dimeric PSD-95 Inhibitors Enters Spinal Cord Tissue 12.1. Method of Spinal Cord Detection of PSD-95 Inhibitors.

The dimeric PSD-95 inhibitors AB143 and AB145 are the 5-FAM-labeled derivatives of AB141 and AB144, respectively (FIG. 4). Hence, AB143 serves as a surrogate compound for investigating the pharmacokinetic properties of AB125/141, while AB145 serves as a surrogate compound for AB144. To investigate if AB143 and AB145 are able to enter spinal cord tissue, they were administered to the mice by intraperitoneal injection (30 mg/kg). The drug-treated mice were decapitated 30 min after injection, and the spinal cord was carefully dissected out, to which 5% trichloroacetic acid (TCA) (300 µL per 0.1 g tissue) was added and the tissue homogenized with an ultrasonic homogenizer (on ice). The homogenated tissue was vortexed and centrifuged for 10 min (20000 g at 4° C.). The supernatant was transferred to a test tube and evaporated, and the residue was reconstituted in water and its fluoresence intensity was determined by using a fluorescence plate reader (excitation/emission:470/525 nm). For quantification of the compounds, a standard curve was prepared by spiking a known amount of AB143 and AB145 into spinal cord tissue from control mice prior to homogenization, followed by work-up and analysis similar to the drug-treated mice.

12.2. PSD-95 Inhibitors are Found in Spinal Cord.

A clear and distinct fluorescence increase was measured in spinal cord tissue from mice treated with AB143 and AB145 compared to saline-treated mice. Based on the standard curve, the concentrations were determined to be 0.061 nmol/g and 0.074 nmol/g of AB143 and AB145, respectively. These concentrations are above the $K_d$ values of the compounds towards PSD-95 (5-10 nM), thereby supporting that both AB143 (and thus AB125) and AB145 (and thus AB144) are able to enter CNS spinal cord tissue at relevant concentrations in order to inhibit PSD-95 and thereby to relieve pain.

TABLE 5

Concentrations of AB143 and AB145 in spinal cord after intraperitoneal injection (30 mg/kg) in mice.

| | AB143 (nmol/g) | AB145 (nmol/g) |
|---|---|---|
| Sample 1 | 0.070 | 0.132 |
| Sample 2 | 0.036 | 0.108 |
| Sample 3 | 0.029 | 0.084 |
| Sample 4 | 0.113 | 0.012 |
| Sample 5 | 0.033 | 0.035 |
| Sample 6 | 0.085 | |
| Average ± SEM | 0.061 ± 0.014 | 0.074 ± 0.022 |

The invention claimed is:

1. A compound comprising a first peptide linked to a second peptide by a linker, wherein the first and the second peptide comprise at least four amide-bonded residues having a sequence YTXV (SEQ ID NO: 5) or YSXV (SEQ ID NO: 6), wherein
   a. Y is selected from among E, Q, and A, and
   b. X is selected from among A, Q, D, N, N-Me-A, N-Me-Q, N-Me-D, and N-Me-N, and
      wherein the linker comprises PEG and, wherein at least one oxygen atom of the PEG is substituted with a nitrogen atom to give NPEG,
      wherein a Cell Penetrating Peptide (CPP) is linked to the nitrogen atom of the linker by an amide bond, and
      wherein the CPP comprises at least 4 amino acid residues selected from arginine and/or lysine.

2. The compound according to claim 1, wherein the linker comprises 4 to 28 ethylene glycol moieties (N=4-28).

3. The compound according to claim 1, wherein the linker is an NPEG-diacid linker, and wherein each carboxyl group of the linker is linked to a terminal residue of the first or the second peptide or peptide analogue.

4. The compound according to claim 1, wherein the CPP comprises a retroinverso peptide.

5. The compound according to claim 1, wherein the CPP is a Tat peptide having amino acid sequence YGRKKRRQRRR (SEQ ID NO: 7) or a Retroinverso-d-Tat peptide having amino acid sequence of rrrqrrkkr (SEQ ID NO: 8).

6. The compound according to claim 1, wherein the first peptide and/or the second peptide is from 5 to 10 amide-bonded residues in length.

7. The compound according to claim 1, wherein the first and/or second peptide is comprised of at least 4 L-amino acid residues.

8. The compound according to claim 1, wherein X is selected from the group consisting of A, Q, and D.

9. The compound according to claim 1, wherein the first peptide and/or the second peptide is N-alkylated.

10. A pharmaceutical composition comprising a compound according to claim 1.

11. A method of treatment of an excitotoxic-related disease in a subject, said method comprising administering to said subject a therapeutically effective amount of the pharmaceutical composition according to claim 10.

12. The method according to claim 11, wherein the disease is ischemic or traumatic injury of the CNS.

13. A method of treatment of pain in a subject, said method comprising administering to said subject a therapeutically effective amount of the pharmaceutical composition according to claim 10.

14. The compound according to claim 1, wherein said compound is selected from the group consisting of:

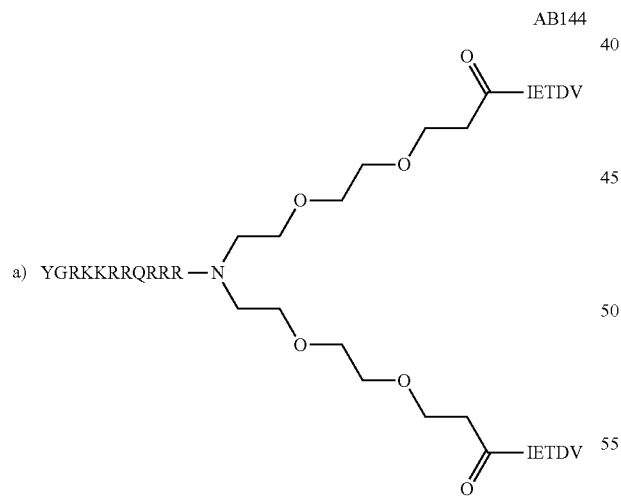

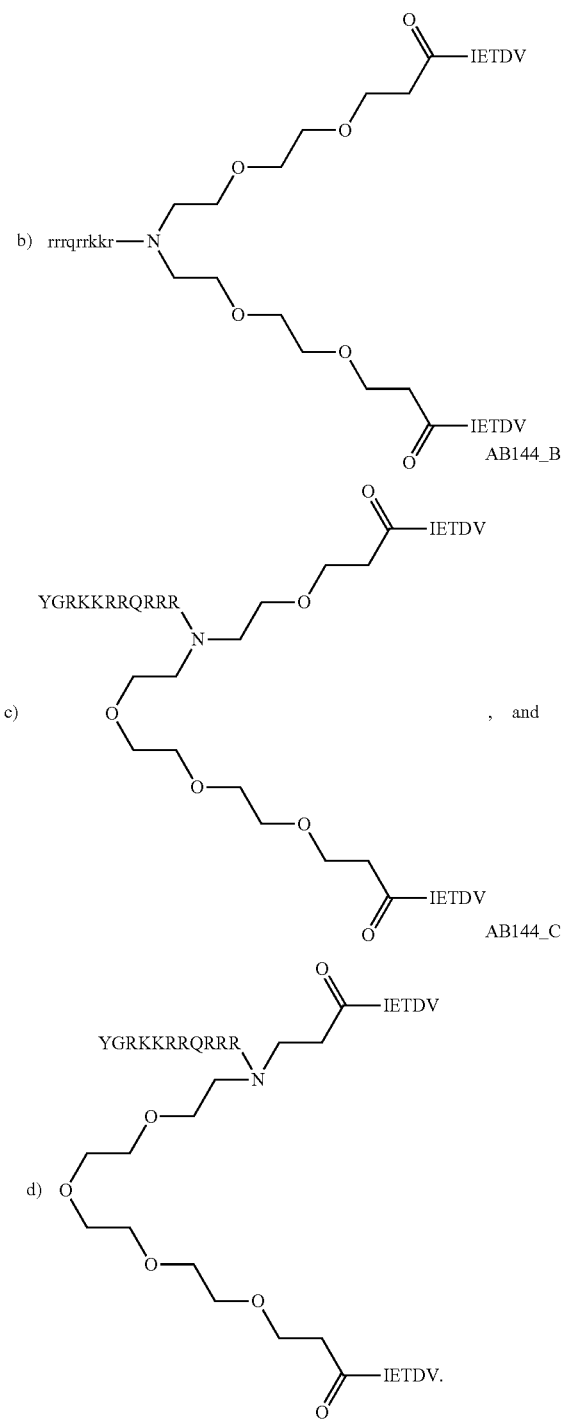

, and

* * * * *

SEQUENCE LISTING

<160> NUMBER OF SEQ ID NOS: 20

<210> SEQ ID NO 1
<211> LENGTH: 605
<212> TYPE: DNA
<213> ORGANISM: Homo sapiens
<220> FEATURE:
<221> NAME/KEY: CDS
<222> LOCATION: (1)..(600)
<223> OTHER INFORMATION: HIS-PDZ1-2 DNA

<400> SEQUENCE: 1

```
atg cac cac cac cac cac ccg cgc gga tcc atg gaa tac gag gaa atc       48
Met His His His His His Pro Arg Gly Ser Met Glu Tyr Glu Glu Ile
1               5                   10                  15 aca ttg gaa agg ggt aac tca ggt ctg ggc ttc agc atc gca ggt ggc       96
Thr Leu Glu Arg Gly Asn Ser Gly Leu Gly Phe Ser Ile Ala Gly Gly
            20                  25                  30 act gac aac cca cac atc ggt gac gac cca tcc att ttc atc acc aag      144
Thr Asp Asn Pro His Ile Gly Asp Asp Pro Ser Ile Phe Ile Thr Lys
        35                  40                  45 atc att cct ggt ggg gct gcg gcc cag gat ggc cgc ctc agg gtc aac      192
Ile Ile Pro Gly Gly Ala Ala Ala Gln Asp Gly Arg Leu Arg Val Asn
    50                  55                  60 gac agc atc ctg ttt gta aat gaa gtg gac gtg cgc gag gtg acc cac      240
Asp Ser Ile Leu Phe Val Asn Glu Val Asp Val Arg Glu Val Thr His
65                  70                  75                  80 tca gcg gcg gtg gaa gcc ctc aaa gag gca ggc tcc atc gtt cgc ctc      288
Ser Ala Ala Val Glu Ala Leu Lys Glu Ala Gly Ser Ile Val Arg Leu
                85                  90                  95 tat gtc atg cgc cgg aag ccc ccg gct gag aag gtc atg gag atc aag      336
Tyr Val Met Arg Arg Lys Pro Pro Ala Glu Lys Val Met Glu Ile Lys
            100                 105                 110 ctc atc aag ggg cct aaa ggt ctt ggc ttc agc atc gca ggg ggc gta      384
Leu Ile Lys Gly Pro Lys Gly Leu Gly Phe Ser Ile Ala Gly Gly Val
        115                 120                 125 ggg aac cag cac atc cca gga gat aat agc atc tat gta aca aag atc      432
Gly Asn Gln His Ile Pro Gly Asp Asn Ser Ile Tyr Val Thr Lys Ile
    130                 135                 140 atc gaa ggg ggt gct gcc cac aag gat ggg agg ttg cag att gga gac      480
Ile Glu Gly Gly Ala Ala His Lys Asp Gly Arg Leu Gln Ile Gly Asp
145                 150                 155                 160 aag atc ctg gcg gtc aac agt gtg ggg cta gag gac gtc atg cat gaa      528
Lys Ile Leu Ala Val Asn Ser Val Gly Leu Glu Asp Val Met His Glu
                165                 170                 175 gat gct gtg gca gcc ctg aag aac acg tat gat gtt gtc tac cta aag      576
Asp Ala Val Ala Ala Leu Lys Asn Thr Tyr Asp Val Val Tyr Leu Lys
            180                 185                 190 gtg gcc aag ccc agc aat gcc tga attcg                                605
Val Ala Lys Pro Ser Asn Ala
        195
```

```
<210> SEQ ID NO 2
<211> LENGTH: 199
<212> TYPE: PRT
<213> ORGANISM: Homo sapiens

<400> SEQUENCE: 2

Met His His His His His Pro Arg Gly Ser Met Glu Tyr Glu Glu Ile
1               5                   10                  15

Thr Leu Glu Arg Gly Asn Ser Gly Leu Gly Phe Ser Ile Ala Gly Gly
            20                  25                  30

Thr Asp Asn Pro His Ile Gly Asp Asp Pro Ser Ile Phe Ile Thr Lys
        35                  40                  45

Ile Ile Pro Gly Gly Ala Ala Ala Gln Asp Gly Arg Leu Arg Val Asn
50                  55                  60

Asp Ser Ile Leu Phe Val Asn Glu Val Asp Val Arg Glu Val Thr His
65                  70                  75                  80

Ser Ala Ala Val Glu Ala Leu Lys Glu Ala Gly Ser Ile Val Arg Leu
                85                  90                  95

Tyr Val Met Arg Arg Lys Pro Pro Ala Glu Lys Val Met Glu Ile Lys
            100                 105                 110

Leu Ile Lys Gly Pro Lys Gly Leu Gly Phe Ser Ile Ala Gly Gly Val
        115                 120                 125

Gly Asn Gln His Ile Pro Gly Asp Asn Ser Ile Tyr Val Thr Lys Ile
130                 135                 140

Ile Glu Gly Gly Ala Ala His Lys Asp Gly Arg Leu Gln Ile Gly Asp
145                 150                 155                 160

Lys Ile Leu Ala Val Asn Ser Val Gly Leu Glu Asp Val Met His Glu
                165                 170                 175

Asp Ala Val Ala Ala Leu Lys Asn Thr Tyr Asp Val Val Tyr Leu Lys
            180                 185                 190

Val Ala Lys Pro Ser Asn Ala
        195

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Tyr Lys Gln Thr Ser Val
1               5

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

Tyr Gly Arg Lys Lys Arg Arg Gln Arg Arg Lys Leu Ser Ser Ile
1               5                   10                  15

Glu Ser Asp Val
            20

<210> SEQ ID NO 5
```

-continued

```
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 5

Tyr Thr Xaa Val
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 6

Tyr Ser Xaa Val
1

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

Tyr Gly Arg Lys Lys Arg Arg Gln Arg Arg Arg
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Arg Arg Arg Gln Arg Arg Lys Lys Arg
1               5

<210> SEQ ID NO 9
<211> LENGTH: 19
<212> TYPE: PRT
<213> ORGANISM: Artificial Sequence
<220> FEATURE:
<223> OTHER INFORMATION: Synthetic peptide

<400> SEQUENCE: 9

Arg Gly Gly Arg Leu Ser Tyr Ser Arg Arg Arg Phe Ser Thr Ser Thr
1               5                   10                  15

Gly Arg Ala

<210> SEQ ID NO 10
<211> LENGTH: 16
<212> TYPE: PRT
<213> ORGANISM: Artificial Sequence
<220> FEATURE:
```

<223> OTHER INFORMATION: Synthetic peptide

<400> SEQUENCE: 10

Arg Gln Ile Lys Ile Trp Phe Gln Asn Arg Arg Met Lys Trp Phe Phe
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide

<400> SEQUENCE: 11

Lys Lys Trp Lys Met Arg Arg Asn Gln Phe Trp Val Arg Val Gln Arg
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: Synthetic peptide

<400> SEQUENCE: 12

Lys Leu Ala Leu Lys Leu Ala Leu Lys Leu Ala Lys Ala Ala Leu Lys
1               5                   10                  15

Ala

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide

<400> SEQUENCE: 13

Tyr Gly Arg Lys Lys Arg Arg Gln Arg Arg Cys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Met His His His His His Pro Arg Gly Ser
1               5                   10

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide

<400> SEQUENCE: 15

Gly Leu Gly Phe
1

<210> SEQ ID NO 16
<211> LENGTH: 5
<212> TYPE: PRT
<213> ORGANISM: Artificial Sequence

```
<220> FEATURE:
<223> OTHER INFORMATION: Synthetic peptide

<400> SEQUENCE: 16

Ile Glu Thr Ala Val
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide

<400> SEQUENCE: 17

Ile Glu Ser Asp Val
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic peptide

<400> SEQUENCE: 18

Ile Glu Thr Asp Val
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide

<400> SEQUENCE: 19

Lys Glu Thr Asp Val
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Lys Ile Glu Thr Asp Val
1               5
```